(12) United States Patent
Li-Sucholeiki et al.

(10) Patent No.: US 7,094,543 B2
(45) Date of Patent: Aug. 22, 2006

(54) METHODS FOR DETECTING RARE POLYMORPHIC VARIANTS IN GENOMIC DNA SEQUENCES

(75) Inventors: Xiao-Cheng Li-Sucholeiki, Winchester, MA (US); Elena Viktorovna Gostjeva, Winchester, MA (US); William G. Thilly, Winchester, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 460 days.

(21) Appl. No.: 10/265,653

(22) Filed: Oct. 4, 2002

(65) Prior Publication Data

US 2003/0143584 A1 Jul. 31, 2003

Related U.S. Application Data

(62) Division of application No. 09/965,662, filed on Sep. 27, 2001, now abandoned.

(60) Provisional application No. 60/235,601, filed on Sep. 27, 2000.

(51) Int. Cl.
*C12Q 1/68* (2006.01)
*C07H 21/02* (2006.01)
*C07H 21/04* (2006.01)

(52) U.S. Cl. .................. 435/6; 536/23.1; 536/24.3
(58) Field of Classification Search .............. 435/6; 536/23.1, 24.3
See application file for complete search history.

(56) References Cited

U.S. PATENT DOCUMENTS

| | | | |
|---|---|---|---|
| 5,045,450 A | 9/1991 | Thilly et al. | |
| 5,633,129 A * | 5/1997 | Karger et al. .................. | 435/6 |
| 5,639,611 A * | 6/1997 | Wallace et al. ................ | 435/6 |
| 5,837,832 A | 11/1998 | Chee et al. | |
| 5,976,842 A | 11/1999 | Wurst | |
| 2003/0092021 A1 | 5/2003 | Thilly | |

FOREIGN PATENT DOCUMENTS

| WO | WO 91/00925 | 1/1991 |
|---|---|---|
| WO | WO 95/21268 | 8/1995 |
| WO | WO 98/40404 | 9/1998 |
| WO | WO 00/34652 | 6/2000 |

OTHER PUBLICATIONS

Bjørheim, J. et al., "Mutations analyses of KRAS exon 1 comparing three different techniques: temporal temperature gradient electrophoresis, constant denaturant capillary electrophoresis and allele specific polymerase chain reaction," *Mut. Res.*, 403:103-12 (1998).

Conneally, P., "Human Genetic Polymorphisms," *Dev. Biol. Stand.*, 83:107-110 (1994).

Cooper, D. and Krawczak, M., "The mutational spectrum of single base-pair substitutions causing human genetic disease: patterns and predictions," *Hum. Genetics*, 85:55-74 (1990).

Crow, J. and Denniston, C., "Mutation in Human Populations," *Adv. Hum. Genet.*, 14:59-77 (1985).

de la Chapelle, A., "Disease gene mapping in isolated human populations: the example of Finland," *J. Med. Genet.*, 30:857-865 (1993).

Ekstrøm, P. et al., "Detection of Low-Frequency Mutations in Exon 8 of the TP53 Gene by Constant Denaturant Capillary Electrophoresis (CDCE)," *BioTechniques*, 27:128-34 (1999).

Ekstrøm, P. et al., "Two-Point Fluorescence Detection and Automated Fraction Collection Applied to Constant Denaturant Capillary Electrophoresis," *BioTechniques*, 29:582-4, 586-9 (2000).

Fält, S. et al., "Identification of in vivo mutations in exon 5 of the human HPRT gene in a set of pooled T-cell mutants by constant denaturant capillary electrophoresis (CDCE)," *Mut. Res.*, 452:57-66 (2000).

Fischer, S. and Lerman, L., "Separation of random fragments of DNA according to properties of their sequences," *Proc. Natl. Acad. Sci USA*, 77:4420-4424 (1980).

Galinsky, D. et al., "Analysis of the apo E/apo C-I, angiotensin converting enzyme and methylenetetrahydrofolate reductase genes as candidates affecting human longevity," *Atherosclerosis*, 129:177-183 (1997).

Gross, E. et al., "A comparison of BRCA 1 mutation analysis by direct sequencing, SSCP and DHPLC," *Hum. Genet.*, 105:72-78 (1999).

Hardelin, J. et al., "Heterogeneity in the mutations responsible for X chromosome-linked Kallmann syndrome," *Hum. Mol. Genetics*, 2:373-377 (1993).

Herrero-Jimenez, P. et al., "Mutation, cell kinetics, and subpopulations at risk for colon cancer in the United States," *Mut. Res.*, 400:553-78 (1998).

Herrero-Jimenez, P. et al., "Population risk and physiological rate parameters for colon cancer. The union of an explicit model for carcinogenesis with the public health records of the United States," *Mut. Res.*, 447:73-116 (2000).

Hovig, E. et al., "Constant denaturant gel electrophoresis, a modification of denaturing gradient gel electrophoresis, in mutation detection," *Mut. Res.*, 262:63-71 (1991).

Kervinen, K. et al., "Apolipoprotein E and B polymorphisms—longevity factors assessed in nonagenarians," *Atherosclerosis*, 105:89-95 (1994).

(Continued)

Primary Examiner—Ethan Whisenant
(74) Attorney, Agent, or Firm—Hamilton, Brook, Smith & Reynolds, P.C.

(57) ABSTRACT

Methods for detecting low frequency nuclear mutations in a target sequence from a genomic DNA sequence are disclosed.

25 Claims, 11 Drawing Sheets

OTHER PUBLICATIONS

Khrapko, K. et al., "Identification of point mutations in mixtures by capillary electrophoresis hybridization," *Nucleic Acids Res.*, 26:5738-40 (1998).

Li-Sucholeiki, X. and Thilly, W., "A sensitive scanning technology for low frequency nuclear point mutations in human genomic DNA," *Nucleic Acids Res.*, 28:i-viii (2000).

Li-Sucholeiki, X. et al., "Applications of constant denaturant capillary electrophoresis / high-fidelity polymerase chain reaction to human genetic analysis," *Electrophoresis*, 20:1224-32 (1999).

Margaglione, M. et al., "Prevalence of Apolipoprotein E Alleles in Healthy Subjects and Survivors of Ischemic Stroke," *Stroke*, 29:399-403 (1998).

Muniappan, B. and Thilly, W., "Application of constant denaturant capillary electrophoresis (CDCE) to mutation detection in humans," *Genet. Anal.*, 14:221-7 (1999).

Tomita-Mitchell, A. et al., "Mismatch repair deficient human cells: spontaneous and MNNG-induced mutational spectra in the HPRT gene," *Mut. Res.*, 450:125-38 (2000).

Tomita-Mitchell, A. et al., "Single nucleotide polymorphism spectra in newborns and centenarians: identification of genes coding for rise of mortal disease," *Gene*, 223:381-391 (1998).

Benzer, S. and Freese, E., "Induction of Specific Mutations with 5-Bromouracil," *Proc. Natl. Acad. Sci. USA*, 44:112-119 (1958).

Cariello, N. et al., "Resolution of a Missense Mutant in Human Genomic DNA by Denaturing Gradient Gel Electrophoresis and Direct Sequencing Using In Vitro Amplification: HRPT$_{Munich}$," *Am. J. Hum. Genet.*, 42:726-734, (1988).

Coller, H. et al., "Mutational Spectra of a 100-Base Pair Mitochondrial DNA Target Sequence in Bronchial Epithelial Cells: A Comparison of Smoking and Nonsmoking Twins[1]," *Cancer Res.*, 58:1268:1277 (1998).

Fischer, S. and Lerman, L., "DNA fragments differing by single base-pair substitutions are separated in denaturing gradient gels: Correspondence with melting theory," *Proc. Natl. Acad. Sci. USA.*, 80:1579-1583 (1983).

Fuchs, R. et al., "Hot spots of frameshift mutations induced by the ultimate carcinogen *N-acetoxy-N*-2-acetylaminofluorene," *Nature*, 294:657-659 (1981).

Harris, C., "p. 53: At the Crossroads of Molecular Carcinogenesis and Risk Assessment," *Science*, 262:1980-1981 (1993).

Khrapko, K. et al., "Constant denaturant capillary electrophoresis (CDCE): a high resolution approach to mutations analysis," *Nucl. Acids Res.*, 22:364-369 (1994).

Khrapko, K. et al., "Mutational Spectrometry: Means and Ends," *Prog. Nucleic Acid Res. Mol. Biol.*, 49:285-311 (1994).

Khrapko, K. et al., "Mutational spectrometry without phenotypic selection: human mitochondrial DNA," *Nucl. Acids Res.*, 25:685-693 (1997).

Khrapko, K. et al., "Mitochondrial mutational spectra in human cells and tissues," *Proc. Natl. Acad Sci. USA*, 94:13798-13803 (1997).

Lerman, L. and Silverstein, K., "Computational Simulation of DNA Melting and Its Application to Denaturing Gradient Gel Electrophoresis," *Meth. Enzymol.*, 155:482-501 (1987).

Li, X.-C. and Thilly, W., "Use of wide-bore capillaries in constant denaturant capillary electrophoresis," *Electrophoresis*, 17:1884-1889 (1996).

Marcelino, L. et al., "Chemically Induced Mutations in Mitochondrial DNA of Human Cells: Mutational Spectrum of *N*-Methyl-*N'*-nitro-*N*-nitrosoguanidine[1]," *Cancer Res.*, 58:2857-2862 (1998).

Miller, J., "Mutational Specificity in Bacteria," *Annu. Rev. Genet.*, 17:215-238 (1983).

Miller, R. and Riblet, R., "Improved phenol emulsion DNA reassociation technique (PERT) using thermal cycling," *Nucl. Acids Res.*, 23:2339-2340 (1995).

Potten, C. and Loeffler, M., "Stem Cells: attributes, cycles, spirals, pitfalls and uncertainties. Lessons for and from the Crypt," *Dev.*, 110:1001-1020 (1990).

Robinson, D. et al., "An analysis of in vivo *hprt* mutant frequency in circulating T-lymphocytes in the normal human population: a comparison for four datasets," *Mut. Res.*, 313:227-247 (1994).

Li-Sucholeiki, X-C. and Thilly, W., "A Sensitive scanning technology for low frequency nuclear point mutations in human genomic DNA," *Nuc. Acids Res.* 28:i-viii (2000).

Thilly, W., "Mutational Spectrometry in Animal Toxicity Testing," *Annu. Rev. Pharmacol. Toxicol.*, 30:369-385 (1990).

Paik, Y., et al., "Nucleotide Sequence and Structure of the Human Apolipoprotein E Gene," *Proc. Natl. Acad. Sci., USA* 82:3445-3449 (1985).

deKnijff, P., et al., "Genetic Heterogeneity of Apolipoprotein E and its Influence on Plasma Lipid and Lipoprotein Levels," *Human Mutation* 4:178-194 (1994).

\* cited by examiner ized gradient gel electrophoresis (DGGE) (Fischer, S. and Lerman, L., 1983. *Proc. Natl. Acad. Sci. USA.*, 80:1579–1583; Cariello, N. et al., 1988. *Am. J. Hum. Genet.*, 42:726–734). However, these methods are tedious and difficult to use. Further, certain common laboratory practices, such as labeling DNA molecules with radioactive phosphorous, create radiolysis reactions that interfere with these methods. Interfering reaction products also arise due to thermolysis in separation extending for many hours at a temperature over 60° C., photochemical reactions with light from ordinary laboratory fluorescent fixtures, and from chemical reactions that presumably involve active oxygen species present in aqueous solutions.

SEQUENCE LISTING

<160> NUMBER OF SEQ ID NOS: 10

<210> SEQ ID NO 1
<211> LENGTH: 30
<212> TYPE: DNA
<213> ORGANISM: Artificial Sequence
<220> FEATURE:
<223> OTHER INFORMATION: probe

<400> SEQUENCE: 1
caaaactgac agcacagaat ccagtggaac       30

<210> SEQ ID NO 2
<211> LENGTH: 30
<212> TYPE: DNA
<213> ORGANISM: Artificial Sequence
<220> FEATURE:
<223> OTHER INFORMATION: probe

<400> SEQUENCE: 2
aagacccaga atggcgctta ggactttggg                                    30

<210> SEQ ID NO 3
<211> LENGTH: 20
<212> TYPE: DNA
<213> ORGANISM: Artificial Sequence
<220> FEATURE:
<223> OTHER INFORMATION: primer
<220> FEATURE:
<221> NAME/KEY: modified_base
<222> LOCATION: (1)...(1)
<223> OTHER INFORMATION: 5'-FITC

<400> SEQUENCE: 3
gaataacaac acaaagaagc                                               20

<210> SEQ ID NO 4
<211> LENGTH: 20
<212> TYPE: DNA
<213> ORGANISM: Artificial Sequence
<220> FEATURE:
<223> OTHER INFORMATION: primer

<400> SEQUENCE: 4
aacaaaaacc ctctaacaag                                               20

<210> SEQ ID NO 5
<211> LENGTH: 123
<212> TYPE: DNA
<213> ORGANISM: Artificial Sequence
<220> FEATURE:
<223> OTHER INFORMATION: primer

<400> SEQUENCE: 5
atmtrtttaa aadadakkaa daatdaaamt aaraaaatth tatgttaatt acaaytgyta   60
tataracatt ttgtttcaaa tgaaayttta aaadactgaa aaattttgta artardtttg  120
att                                                               123

<210> SEQ ID NO 6
<211> LENGTH: 20
<212> TYPE: DNA
<213> ORGANISM: Artificial Sequence
<220> FEATURE:
<223> OTHER INFORMATION: primer
<220> FEATURE:
<221> NAME/KEY: modified_base
<222> LOCATION: (18)...(18)
<223> OTHER INFORMATION: Fluorescein

<400> SEQUENCE: 6
ccatctcaga tcccaactcc                                               20

<210> SEQ ID NO 7
<211> LENGTH: 36
<212> TYPE: DNA
<213> ORGANISM: Artificial Sequence
<220> FEATURE:

```
<223> OTHER INFORMATION: primer

<400> SEQUENCE: 7
aacaaaaacc ctctaacaag aatcaaacct acttac                              36

<210> SEQ ID NO 8
<211> LENGTH: 20
<212> TYPE: DNA
<213> ORGANISM: Artificial Sequence
<220> FEATURE:
<223> OTHER INFORMATION: primer

<400> SEQUENCE: 8
tataatctag aaatgattga                                                20

<210> SEQ ID NO 9
<211> LENGTH: 20
<212> TYPE: DNA
<213> ORGANISM: Artificial Sequence
<220> FEATURE:
<223> OTHER INFORMATION: primer

<400> SEQUENCE: 9
accgttaact tccaattaac                                                20

<210> SEQ ID NO 10
<211> LENGTH: 20
<212> TYPE: DNA
<213> ORGANISM: Artificial Sequence
<220> FEATURE:
<223> OTHER INFORMATION: primer

<400> SEQUENCE: 10
gcgggcgcag ggaaagaggt                                                20
```

METHODS FOR DETECTING RARE POLYMORPHIC VARIANTS IN GENOMIC DNA SEQUENCES

RELATED APPLICATION

This application is a divisional application of U.S. patent application Ser. No. 09/965,662, filed on Sep. 27, 2001, now abandoned which claims the benefit of U.S. Provisional Application No. 60/235,601, filed on Sep. 27, 2000.

The entire teachings of the above applications are incorporated herein by reference.

GOVERNMENT SUPPORT

The invention was supported, in whole or in part, by grants P30-ESO2109, P01-ESO3926, P01-ESO7168 and P42-ESO4675 from the National Institute for Environmental Health Sciences. The Government has certain rights in the invention.

BACKGROUND OF THE INVENTION

Most human inherited diseases and cancers are known to be caused by mutations in nuclear genes. In general, a mutation is considered to be particular polymorphic variants at a genetic locus. The mutation can be a single nucleotide difference, often referred to as a point mutation. Determination of mutational spectra in disease-related genes in non-tumor tissues can provide direct evidence as to whether a specific mutagenic agent or pathway is involved in a particular human disease. In the field of genetic epidemiology, for example, it is useful to be able to detect patterns in the frequencies of genetic polymorphisms (e.g., mutations) that are indicative of the causes of disease. In the field of pediatric genetics, detection of polymorphisms is useful to screen for early diagnosis of rare genetic diseases in newborns. In genetic counseling of prospective parents, detection of polymorphisms in their cells is anticipated to be of significant predictive value in determining the quality of life for newborns. In addition, the detection of polymorphisms can be useful in the development of pharmaceuticals, such as vaccines or recombinant proteins. The detection of polymorphisms is also useful in toxicological studies to determine if genetic damage has occurred due to specific agents, such as additives in cosmetics or environmental contaminants.

At the cellular and tissue level, polymorphisms at a specific genetic locus may give rise to significantly altered cellular behavior. However, because even relatively small cell or tissue samples can contain millions or billions of DNA molecules containing the particular genetic locus, an examination of the mutational spectra, a representation of the range and frequencies of polymorphic variants at a genetic locus, requires detecting alleles that are potentially present at a very low frequency. In fact, since many pathological conditions manifest themselves even where only a small fraction of the DNA is mutated, it is probable that detection of the rare alleles is important for the early detection of many pathological disorders. For example, the ability to detect cancer cells by virtue of a polymorphism present in a small fraction of cells within a tissue or blood sample can be useful to detect metastasis of the cancer, to use as a signal that the cancer is recurring, or as a screen for the initial appearance of a cancer. Additionally, determining the mutational spectra of, for example, the tumor suppressor gene, p53, in non-tumor tissue of a tumor bearing organ may lead to identification of the probable cause of a tumor (Harris, C., 1993. *Science*, 262:1980–1981).

A number of methods have been used to detect mutant DNA sequences, including isolation of DNA from cells, cloning and sequencing the cloned product. Several electrophoretic methods have been used to separate mutant DNA from wild-type DNA including, for example, denaturing As methods for detecting polymorphisms currently known in the art do not allow for the detection of rare polymorphisms in relatively small samples, the present state of the art can not allow for detection of rare mutations in, for example, stem cells. Thus, a fast and reproducible method that can detect mutant DNA sequences present in a sample, including mutant DNA sequences that occur as a small fraction of DNA molecules relative to the total number of DNA molecules present in a sample, would be very important.

SUMMARY OF THE INVENTION

The present invention relates to methods for enriching molecules containing (e.g., comprising) target sequences in a DNA sample and detecting one or more polymorphisms in the target sequences. The methods of the present invention encompass enriching for, and detecting, rare mutations occurring at a low frequency (e.g., polymorphic alleles present at a fraction found with as low as $10^{-6}$ per bp in the sample). In particular, as described herein, a novel strategy has been employed to first isolate a nuclear target sequence from genomic DNA and to achieve a higher enrichment of mutants (e.g., sequences that contain polymorphic variants) relative to non-mutant (e.g., wild-type) sequences in the sample prior to subjecting the sample to a method of detecting the mutation, for example, by amplification and processing by, for example, wide bore constant denaturant capillary electrophoresis (CDCE).

In one embodiment, the present invention is directed to a method for detecting low frequency mutations in a target sequence from a DNA sample including the steps of: enriching a DNA sample for one or more target sequences, wherein the enrichment step comprises sequence-specific hybridization to the target sequences with one or more labeled probes, wherein each labeled probe is complementary to a specific target sequence, resulting in about a $10^3$-fold to about a $10^4$-fold enrichment of target sequences from the DNA sample thereby obtaining a target-enriched sample; and detecting mutations in the target sequence or sequences from the target-enriched sample. The enrichment step can also include: denaturing double-stranded DNA; contacting the denatured DNA with one or more probes comprising a sequence complementary to one or more target sequences to form a mixture; maintaining the mixture under conditions such that probe-fragment hybrid molecules are formed; and isolating the probe-fragment hybrids from the mixture, resulting in a target-enriched sample and a depleted sample. In a particular embodiment, the DNA sample fragmented prior to denaturation.

The present invention can utilize a probe complementary to a specific target sequence such that the probe has an affinity moiety unique for a specific target sequence. In this embodiment, a plurality (i.e., multiple) of target sequences can be concurrently enriched from a sample resulting in a plurality of target-enriched DNA samples. The remainder of the sample, the "depleted" sample, can be subjected to a subsequent enrichment step to enrich for one or more target sequences different from the target sequences obtained in the first enrichment step. One of skill in the art will recognize that either single-stranded or double-stranded DNA samples are suitable for the methods of the present invention.

In one embodiment, constant denaturant capillary electrophoresis can be used to detect nuclear mutations. In another embodiment, allele-specific polymerase chain reaction is used to detect nuclear mutations. Methods of the present invention can be used to detect mutations present at a mutant fraction about or higher than $10^{-6}$.

In one embodiment, the present invention is directed to a method for detecting low frequency nuclear mutations in a target sequence from a DNA sample including the steps of: enriching the DNA sample for molecules comprising one or more target sequences thereby preparing a target-enriched sample comprising mutant and non-mutant sequences, wherein the enrichment step comprises sequence-specific hybridization with one or more labeled probes that hybridize to the target sequences resulting in about a $10^3$-fold to about $10^4$-fold enrichment of molecules comprising target sequences from the DNA sample; subjecting the target-enriched sample to constant denaturant capillary electrophoresis using a wide-bore capillary to separate mutant heteroduplexes from non-mutant homoduplexes; amplifying the heteroduplexes of step b) by high fidelity polymerase chain reaction to obtain amplified polymerase chain reaction products; subjecting the polymerase chain reaction products of step c) to constant denaturant capillary electrophoresis to further enrich the sample for mutants, thereby creating a mutant-enriched sample; subjecting the mutant-enriched sample of step d) to constant denaturant capillary electrophoresis to obtain a mutational spectra; and selecting one or more individual mutant fractions from the mutational spectra for sequence analysis to detect mutations.

In one embodiment, step b) can include subjecting mutant heteroduplexes to capillary electrophoresis prior to hifiPCR. In another embodiment, step d) can include subjecting the first enriched pool to one or more additional rounds of CDCE prior to obtaining the mutational spectra. In a particular embodiment, the mutation detected is present at a mutant fraction about or higher than $10^{-6}$.

The genomic DNA can be fragmented to obtain double-stranded DNA fragments. In embodiments with fragmented DNA, the double-stranded DNA fragments are enriched for fragments comprising one or more target sequence. The enrichment step includes: a) denaturing the double-stranded DNA fragments; b) contacting the denatured fragments with a probe comprising a sequence complementary to a known target sequence; c) maintaining the probe and DNA fragments under conditions such that a probe-fragment hybrid molecule is formed; d) isolating the probe-fragment hybrid; and e) regenerating a double-stranded fragment, thereby generating an enriched pool of DNA fragments. The enrichment step can be accomplished using a probe comprising (e.g., labeled with) an affinity moiety. Isolation of the probe-fragment hybrid can be accomplished by binding, or contacting, the probe-fragment hybrid to a binding partner molecule affixed to a solid support matrix, wherein the binding partner molecule binds to the affinity moiety of the probe.

In another embodiment, the present invention is directed to a method of mutational analysis to detect nuclear gene mutations at mutant fractions at or above $10^{-6}$ in a target sequence comprising subjecting a genomic DNA sample comprising one or more target sequences to CDCE and hifiPCR to obtain a mutational spectrum to detect nuclear gene mutations, wherein, prior to CDCE and hifiPCR, the genomic DNA sample is enriched for a target sequence and wherein the enrichment includes two steps: a) a sequence-specific hybridization coupled with a biotin-streptavidin capture system to enrich for DNA molecules comprising the target sequences; and b) CDCE using a wide bore capillary.

In another embodiment, the invention is directed to a method for preparing a plurality of target-enriched DNA samples, wherein each enriched DNA sample includes one or more particular target sequences. The enrichment method includes: contacting a DNA sample with a plurality of probes that can hybridize to a plurality of target sequences under conditions suitable for hybridization, wherein each probe that hybridizes to a specific target sequence comprises an affinity moiety wherein the affinity moiety is unique for each target sequence, thereby forming a hybridized sample mixture containing a plurality of affinity-labeled target sequences; contacting the hybridized sample mixture with a plurality of binding partners to the affinity moieties, wherein each binding partner is attached to a particular solid support matrix and wherein each binding partner binds to a specific affinity moiety; and separating the particular solid support matrices, thereby separating the particular target sequences, resulting in separate target-enriched DNA samples. The present invention enables DNA samples to be concurrently enriched for a plurality of target sequences. At least one paramagnetic solid support and at least one non-magnetic solid support can be used. In another embodiment, at least one fluorescently-labeled solid support can be used and separated based on differences in fluorescence. The target enriched sample can then be mutant-enriched by, for example, constant denaturant capillary electrophoresis or allele-specific polymerase chain reaction.

As described herein, the methods of the present invention comprise a mutation detection assay with a 10- to 100-fold improved sensitivity, allowing for the detection of mutations having a mutant fraction of $10^{-6}$ or higher, which enables the detection of mutations that can occur in, for example, stem cells.

BRIEF DESCRIPTION OF THE DRAWINGS

FIG. 8 is a graphical representation of CE separations of fluorescein-labeled mismatch amplification products amplified from different lung sectors mixed with known copies of internal standards. The peak labels are as in FIG. 7. The name of each sector indicates its anatomic position in the upper bronchial tree: LUL, left upper lobe; LLL, left lower lobe; RUL, right upper lobe; RLL, right lower lobe; RUL, right upper lobe; MC, main carina; Trac, trachea. The value of R is the ratio of the peak area of Mut2(3) to that of Std2(3). The initial mutant number ($N_{mut}$) in each sector is calculated as:

$$N_{mut} = (R * N_{std} - 10^{-5} * N_{wt})/f$$

Where $N_{std}$ is the copy number of the internal standard introduced prior to PCR; $N_{wt}$ is the copy number of the wild-type sequence in the sector, f is the fraction of the sector that was subjected to the assay.

Figure 9:
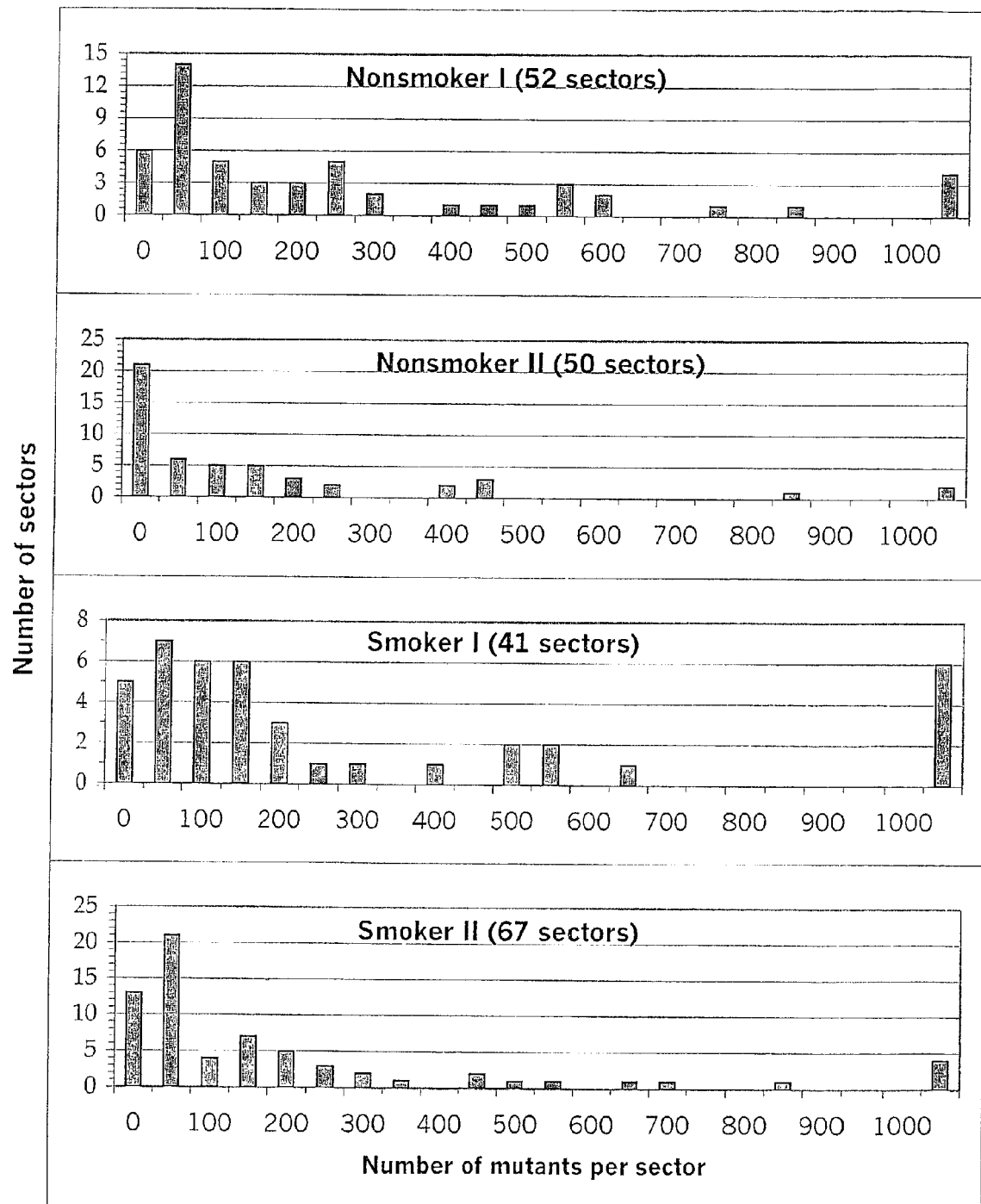

FIG. 9 is a graphical representation of the distribution of p53 bp 746 G->T mutants among lung sectors.

Figure 10:
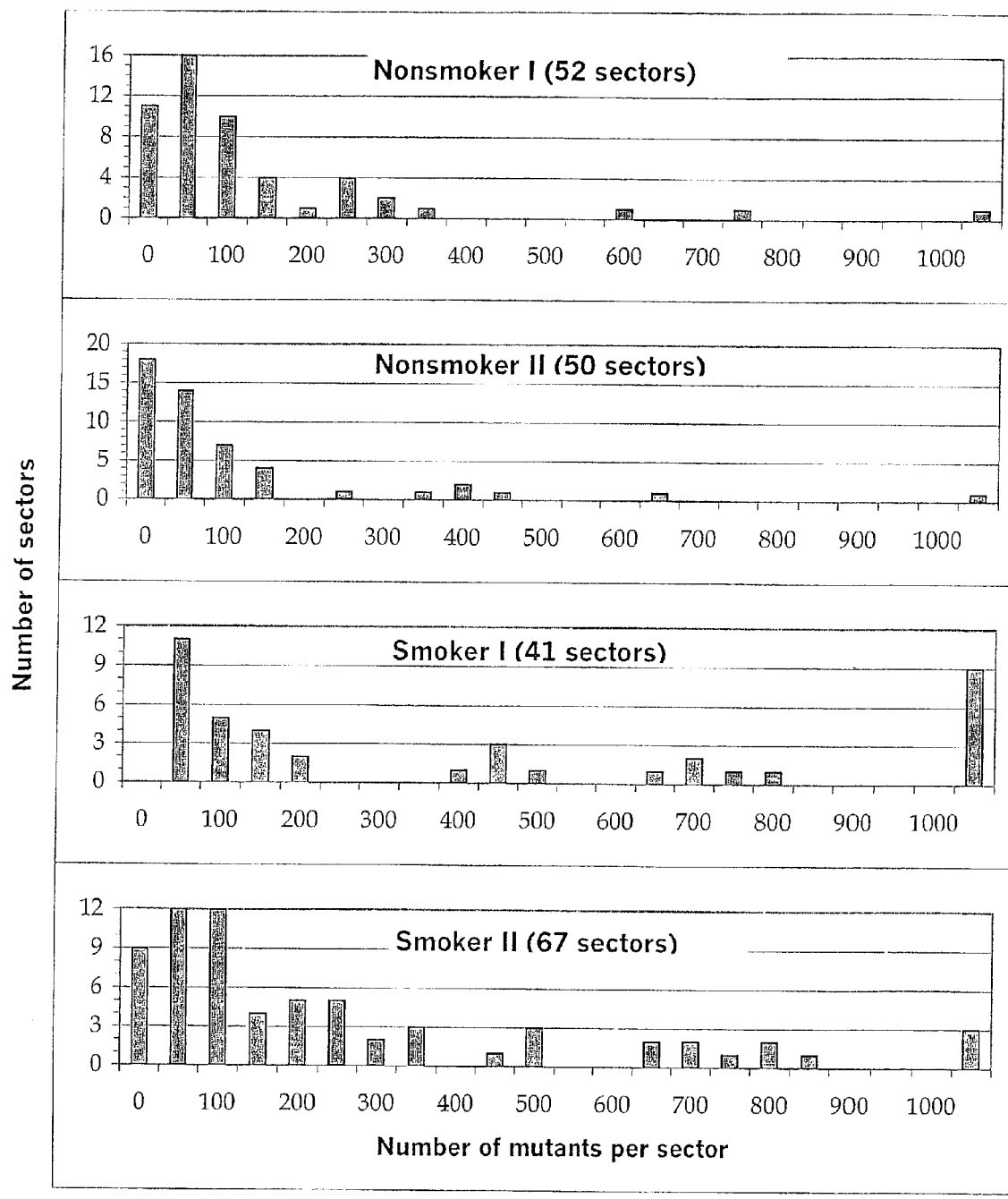

FIG. 10 is a graphical representation of the distribution of p53 bp 747 G->T mutants among lung sectors.

DETAILED DESCRIPTION OF THE INVENTION

Most human inherited diseases and cancers are known to be caused by mutations in nuclear genes. However, the methodologies used in previous studies of mutational spectra are based on phenotypic selection, in which rare mutant cells are recognized and isolated on the basis of an altered phenotype conferring the ability to grow under selective conditions (Benzer, S. and Freese, E., 1958. *Proc. Natl. Acad. Sci. USA*, 44:112–119; Miller, J., 1983. *Annu. Rev. Genet.*, 17:215–238; Fuchs, R. et al., 1981. *Nature*, 294: 657–659; Thilly, W., 1990. *Annu. Rev. Pharmacol. Toxicol.*, 30:369–385; Khrapko, K. et al., 1994. *Prog. Nucleic Acid Res. Mol. Biol.*, 49:285–311). Such methods preclude analysis of genes for which selective conditions cannot be devised in single cell systems. They also preclude analysis of any gene in some human tissues since the cells cannot yet be grown in culture.

To overcome these limitations to mutational spectrometry, means to "select" rare mutants based on differences in the cooperative melting behavior between wild-type and mutant DNA sequences have been developed (Khrapko, K. et al., 1994. *Prog. Nucleic Acid Res. Mol. Biol.*, 49:285–311; Khrapko, K. et al., 1994. *Nucl. Acids Res.*, 22:364–369).

These efforts exploit small differences in DNA melting temperatures to create clear and discernible differences in the electrophoretic mobility of DNA during migration through a gel matrix under partially denaturing conditions (Fischer, S. and Lerman, L., 1983. *Proc. Natl. Acad. Sci. USA,* 80:1579–1583.). That approach has been extended for constant denaturant capillary electrophoresis (CDCE), which, in combination with hifiPCR, allows for scanning for point mutations in a 100-bp mitochondrial DNA sequence in human cells and tissues. Reproducible mitochondrial point mutational hotspots were discovered at frequencies from $10^{-5}$ to greater than $10^{-4}$ (Khrapko, K. et al, 1997. *Proc. Natl. Acad. Sci. USA,* 94:13798–13803; Coller, H. et al., 1998. *Cancer Res.,* 58:1268–1277; Marcelino, L. et al., 1998. *Cancer Res.,* 58:2857–2862).

The criterion for an assay of sufficient sensitivity to detect nuclear mutations differs among tissues. Studies in peripheral T-lymphocytes have shown that the average mutant fraction in the nuclear HPRT and HLA loci is about $10^{-8}$ per bp in middle aged humans (Robinson, D. et al., 1994. *Mut. Res.,* 313:227–247; Potten, C. and Loeffler, M., 1990. *Dev.,* 110:1001–1020.). However, mutations are not randomly distributed over DNA sequences but occur more frequently at "hotspots." Such hotspots have mutant fractions 10 or 100 times higher than the average for all base pairs. One would expect that mutations at these nuclear hotspots would occur at mutant frequencies in the range of $10^{-7}$ to somewhat greater than $10^{-6}$, depending on the specific sample tissue.

Cell replacement in adult mammalian tissues takes place via discrete unit of proliferation termed "turnover unit." A turnover unit is defined by one stem cell and its descendant transition and terminal cells. Mutations that occur in a stem cell would be both maintained in the stem cell and subsequently transmitted to the descendant cells, thus giving rise to a mutant colony with the size of a turnover unit. The turnover unit size is estimated to be about 128 cells in rat mammary glands and about 256 cells in human lung epithelium. Different tissues would be expected to have turnover units of different sizes. For mutational analysis, anatomically distinct sectors can be excised from most tissues and analyzed in series. If the turnover unit consists of 100 or more cells and each tissue sector is dissected to contain about $0.5 \times 10^8$ cells (or $10^8$ gene copies), the expected mutant fraction would be $10^{-6}$. Thus a mutation assay with a sensitivity of $10^{-6}$ would permit the detection of mutations that have occurred in stem cells.

The application of a prior CDCE method, previously the most sensitive detection method, to nuclear genes was not straightforward. Both the cellular copy numbers and the point mutant fractions of nuclear genes are several hundred-fold lower than those of the mitochondrial DNA. In practical terms, this means samples consisting of a few micrograms of DNA are sufficient to reproducibly detect mitochondrial mutational hotspots at fractions of $10^{-5}$–$10^{-4}$, but several milligrams of genomic DNA (gDNA) would be required to reproducibly detect nuclear hotspots at fractions of $10^{-6}$. It was clear that the mutational analysis of nuclear genes to identify rare polymorphisms required significant technical improvements on both the detection sensitivity and the sample-handling capacity of previous approaches.

The present invention encompasses methods for identifying these rare polymorphisms in biological samples. As described herein, a high degree of sensitivity was achieved by employing new strategies to first isolate the desired target sequence from genomic DNA and then to achieve a higher enrichment of mutants against the non-mutant (e.g., wild-type) sequences prior to PCR. Any biological sample that contains genomic, nuclear, mitochondrial, chloroplast or other DNA is suitable for use in the methods of the present invention. For example, a DNA sample (nuclear, mitochondrial, chloroplast, pooled) can be obtained from an individual, e.g., a human or other organism. DNA can also be obtained from animals, plants or microbes. In one embodiment, DNA is isolated from a sample of cells, consisting of from about $10^6$ to about $10^{10}$ cells, derived from one or more individuals in a population. Generally, a sample (e.g., any DNA-containing biological sample such as a tissue biopsy, whole blood, isolated cells, cultured cells) is obtained and DNA is isolated from the cells contained in the sample. DNA can be isolated from a sample from an individual or from pooled samples. For example, DNA can be obtained by acquiring a sample of white blood cells of other suitable tissue sample from each individual of a population. Samples containing similar numbers of cells can be pooled and DNA can be isolated therefrom. Several samples of DNA isolated from individuals can also be pooled.

A major technical challenge for detecting low frequency mutations in single-copy nuclear genes has been the large quantity of genomic DNA required. As used herein, "low frequency" refers to frequencies at about $10^{-6}$ or higher. In many cases, large quantities of DNA are difficult to obtain. This limitation impedes the performance of most mutation detection methods. In the methods provided herein, the amount of DNA required is significantly reduced by employing a strategy to highly enrich the desired nuclear DNA molecules from genomic DNA. In addition, DNA in the sample that remains after the enrichment step (e.g., the "depleted" or "residual" sample) can be recovered and used for other assays and detection strategies. In one embodiment, the enrichment strategy is sequence-specific as illustrated in Example 2, which describes enrichment of a 482 bp APC gene fragment. By monitoring, for example, the copy numbers of the APC target fragment and a 205 bp mitochondrial DNA sequence used as a reference, the experimental conditions (including the hybridization temperature, the molar ratio of probe/target, the quantities of paramagnetic beads and the hybrid-bead binding conditions) can be adjusted to obtain both a high level of target sequence yield and enrichment. The copy numbers of the two sequences can be measured in the initial genomic DNA sample and the final target-enriched sample based on competitive PCR followed by constant denaturant capillary electrophoresis (CDCE) separation. In Example 2, after the enrichment procedure under the optimal conditions, the molar ratio of the APC target sequence to the mitochondrial DNA sequence was found to increase from $1/(321\pm55$; 95% confidence intervals) in the initial genomic DNA samples to $32\pm12$ in the final elutions, resulting in about $10^4$-fold enrichment of the target relative the target sequence was measured and found to be $74\pm7\%$.

The first enrichment step can be optimized, as shown in Example 2, where the isolated DNA sample is fragmented using methods well known to those of skill in the art (e.g., digestion with one or more suitable restriction endonuclease, physical shearing). For example, any restriction endonuclease that does not cleave within the target region of the DNA can be used. Preferably, a restriction endonuclease that cuts DNA with low frequency is selected, such as an enzyme with a 6 base pair recognition site ("six-cutter"). Six-cutter enzymes are less likely to cut a target sequence than other enzymes which cut DNA with higher frequency (e.g., four-cutters) and convert genomic DNA into a pool of fragments averaging about 4000 bp. However the DNA sample is fragmented, one of skill in the art will recognize that a fragmented pool can be created and the average length of fragments in the pool can be readily manipulated. DNA can be individually digested, and the resulting fragments pooled, or a pooled sample of DNA can be digested with a suitable restriction endonuclease to produce a pool of fragments.

Figure 2:
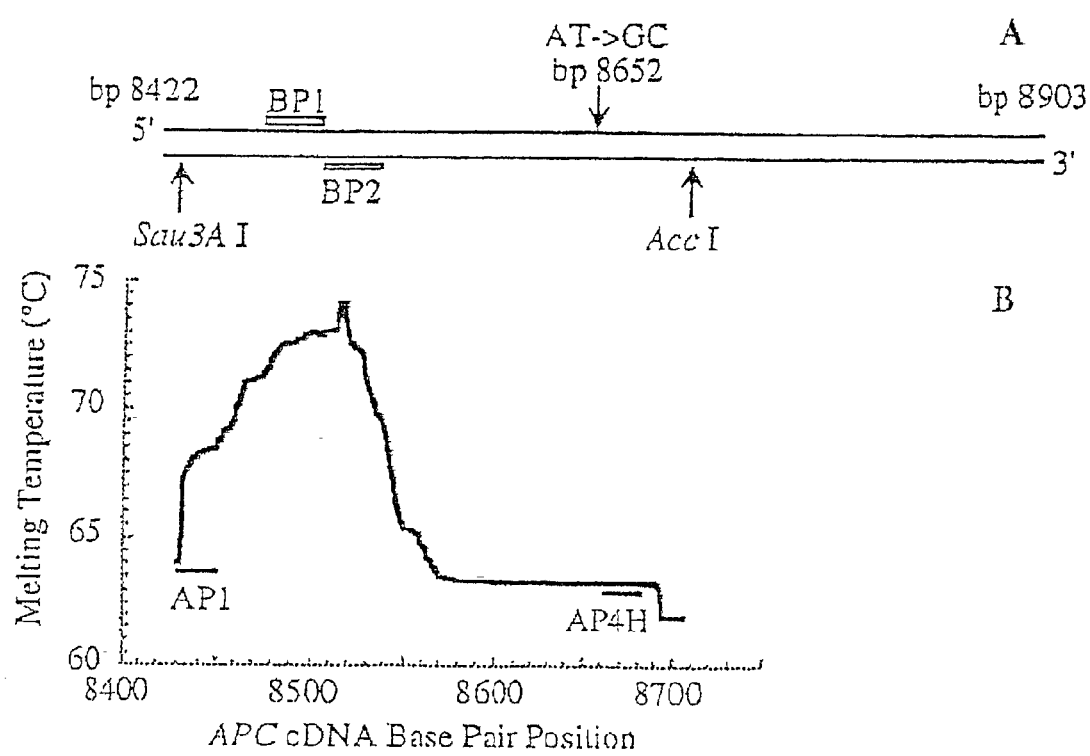
FIGS. 2A and 2B are schematic and graphical representations of the physical properties of an APC gene fragment. (A) The 482 bp APC gene fragment (APC cDNA bp 8422–8903; GenBank accession number: XM-043933) released by digestion of human genomic DNA with endonucleases Haeff and XbaI. The positions of the two biotinylated 30-mer probes (BP1 and BP2, SEQ ID NOS.: 1 and 2, respectively) for enriching this fragment from genomic DNA are indicated by open bars. The positions of the AT–>GC transition at APC cDNA bp 8652 carried by the internal standard and the recognition sites of endonucleases Sau3AI and AccI used to liberate the 271 bp APC gene fragment (APC cDNA bp 8434–8704) are indicated by arrows. (B) The melting profile of the 271 bp APC gene fragment calculated according to a melting algorithm (Lerman, L. and Silverstein, K., 1987. *Meth. Enzymol.*, 155: 482–501). The positions of the primers (AP1 and AP4H; SEQ ID NOS.: 3 and 4, respectively) used in hifiPCR are indicated by filled bars.

In Example 2, the target-enriched sample was restriction digested to release the 271 bp APC fragment suitable for CDCE separation (FIG. 2B). The sample was then desalted and concentrated by ultrafiltration in order to be completely electro-injected onto the capillary column. This procedure produced a yield of 50–60%. Thus, an initial sample of 3 mg genomic DNA (gDNA) from $3 \times 10^8$ MT1 cells was reduced to less than 1 µg containing about $2 \times 10^8$ copies of the target sequence ($6 \times 108 \times 74\% \times 50\%$). Based on the yield of the subsequent CE separations of almost 100% and the estimated efficiency of the first cycle PCR of 0.5, any mutant at an initial mutant fraction of $10^{-6}$ in the sample is represented by a minimum of 100 mutant copies in the present procedures. A sample of this size permits measurement of the cellular mutants at or above $10^{-6}$ with an expected numerical variation of about ±20% (Poisson distribution, 95% confidence limits). Many suitable methods for isolating DNA from cells and/or tissues are available.

The pool of DNA fragments derived from a sample of an individual in a population is, enriched for specific fragments of interest ("target fragments" or "target sequences") containing specific sequences, thus creating an enriched pool of DNA fragments and a depleted (i.e., residual) sample of fragments. The depleted/residual sample does not contain target sequences contained in the enriched sample. One of skill in the art will recognize that the methods described herein can be used with either single-stranded DNA samples or double-stranded DNA samples. For example, the target sequence described in Example 2, in which mutations can be detected, comprises 121 base pairs (APC cDNA bp 8543–8663) within the low melting domain. More generally, particular sequences at particular chromosomal loci can be isolated. In other embodiments, one or more specific coding sequence(s) can be enriched in the fragmented pool (also referred to herein as a sample). In other embodiments, fragments containing particular sequence elements (e.g., promoters, regulatory elements, DNA binding protein DNA binding sites, repetitive elements and the like) can be enriched. The target-enriched pool of DNA fragments, therefore, contains fragments with specific properties of interest (e.g., sequence elements) that were selected during the enrichment process. Fragments that do not contain such properties of interest are eliminated from the pool and remain in the depleted pool.

In the methods described herein, the enrichment step is performed to enrich for fragments of interest based on known sequence elements. For example, fragments containing one or more specific coding sequences can be enriched. Due to the large size of the genome relative to specific sequences of interest, enriching for fragments containing sequences of interest could potentially eliminate >99% of the fragments in the pool of DNA fragments. If DNA is isolated from a sample containing 10,000 human diploid cells, each cell containing two copies of the human genome (approximately $3 \times 10^9$ bases), a pool of approximately $1.2 \times 10^{10}$ fragments with an average length of 5,000 bases would be produced. If a specific coding sequence of, for example, 1,000 bases in length, was of interest to be enriched, an isolation of all fragments containing all or part of this coding sequence would involve the isolation of approximately 22,000 fragments (assuming random fragmentation, approximately 9.1% of the fragmentation events would lead to two fragments containing part of the coding sequence). Enriching for these 22,000 fragments would provide an expected enrichment of approximately $5 \times 10^5$-fold of the fragments of interest versus the total pool of DNA fragments. In addition to coding sequences, sequence elements of interest can include: regulatory elements such as, for example, promoters, enhancer binding sites, repressor binding sites, and the like; repeat elements; splice sites; intron sequences; or any other known sequence element.

In one embodiment of the present invention, fragments are isolated based on specific known sequence elements. Such enrichment is also referred to herein as "affinity enrichment." If a sequence is known, a probe can be synthesized such that the probe is complementary to part or all of the sequence of interest. The probe can be synthesized to contain an affinity moiety, e.g., biotin, thiolate, antigenic domains, fluorescent moieties and the like, or other physical property so as to allow for the specific isolation of the probe. If multiple (e.g., a plurality) of affinity-labeled probes are used, as in the case when one is enriching multiple target sequences concurrently from a DNA sample, each probe can be labeled in such a manner such that one set of probes binds to a specific target sequence and another set of probes binds to a different target sequence, and so forth for as many target sequences there are to be enriched from the sample.

Affinity moieties typically have binding partners (e.g., biotin is bound by steptavidin or avidin, disulfide bonds are bound by thiolate, etc.), but, as used herein, can refer to moieties that allow for specific isolation as well (e.g., fluorescent moieties that allow for separation based on fluorescent properties). A pool of DNA fragments that has been denatured can then be contacted with copies of the probe (preferably, the number of copies of probes is in excess of the number of fragments containing the sequence of interest). If the solution containing this mixture of fragments and probes is then altered to allow for hybridization (e.g., by lowering the temperature), partially double-stranded molecules will be formed (a "probe-fragment hybrid") containing a fragment and a copy of a probe hybridized to the sequence of interest on the fragment. Probes can be designed such that hybridization under low, moderate, or highly stringent conditions can occur upon contact with complementary sequences. For example, hybridization at a temperature 5–10° C. less than the melting temperature ($T_m$) of the hybrid in 4×SSC buffer could be considered to be a low stringency hybridization condition.

In Example 2, the genomic DNA was heat denatured and hybridized simultaneously with excess biotin-labeled oligonucleotide probes targeted to the Watson and Crick strands of the desired sequence. The hybrids were captured by streptavidin-coated paramagnetic beads and magnetically separated from the bulk DNA solution. The target fragments were then eluted from the beads by heating and subsequently reannealing to form double-strands. One of skill in the art will recognize that probes can be pre-loaded onto a solid support matrix prior to hybridization or subsequent to hybridization.

Conditions for stringency are shown in the table below which (Jacobs et al., WO98/40404). Highly stringent conditions are those that are at least as stringent as, for example, conditions A–F; stringent conditions are at least as stringent as, for example, conditions G–L; and reduced stringency conditions are at least as stringent as, for example, conditions M–R.

TABLE 1

Hybridization conditions.

| Stringency Condition | Polynucleotide Hybrid | Hybrid Length (bp)‡ | Hybridization Temperature and Buffer† | Wash Temperature and Buffer† |
|---|---|---|---|---|
| A | DNA:DNA | ≥50 | 65° C.; 1xSSC -or- 42° C.; 1xSSC, 50% formamide | 65° C.; 0.3xSSC |
| B | DNA:DNA | <50 | $T_B$*; 1xSSC | $T_B$*; 1xSSC |
| C | DNA:RNA | ≥50 | 67° C.; 1xSSC -or- 45° C.; 1xSSC, 50% formamide | 67° C.; 0.3xSSC |
| D | DNA:RNA | <50 | $T_D$*; 1xSSC | $T_D$*; 1xSSC |
| E | RNA:RNA | ≥50 | 70° C.; 1xSSC -or- 50° C.; 1xSSC, 50% formamide | 70° C.; 0.3xSSC |
| F | RNA:RNA | <50 | $T_F$*; 1xSSC | $T_F$*; 1xSSC |
| G | DNA:DNA | ≥50 | 65° C.; 4xSSC -or- 42° C.; 4xSSC, 50% formamide | 65° C.; 1xSSC |
| H | DNA:DNA | <50 | $T_H$*; 4xSSC | $T_H$*; 4xSSC |
| I | DNA:RNA | ≥50 | 67° C.; 4xSSC -or- 45° C.; 4xSSC, 50% formamide | 67° C.; 1xSSC |
| J | DNA:RNA | <50 | $T_J$*; 4xSSC | $T_J$*; 4xSSC |
| K | RNA:RNA | ≥50 | 70° C.; 4xSSC -or- 50° C.; 4xSSC, 50% formamide | 67° C.; 1xSSC |
| L | RNA:RNA | <50 | $T_L$*; 2xSSC | $T_L$*; 2xSSC |
| M | DNA:DNA | ≥50 | 50° C.; 4xSSC -or- 40° C.; 6xSSC, 50% formamide | 50° C.; 2xSSC |
| N | DNA:DNA | <50 | $T_N$*; 6xSSC | $T_N$*; 6xSSC |
| O | DNA:RNA | ≥50 | 55° C.; 4xSSC -or- 42° C.; 6xSSC, 50% formamide | 55° C.; 2xSSC |
| P | DNA:RNA | <50 | $T_P$*; 6xSSC | $T_P$*; 6xSSC |
| Q | RNA:RNA | ≥50 | 60° C.; 4xSSC -or- 45° C.; 6xSSC, 50% formamide | 60° C.; 2xSSC |
| R | RNA:RNA | <50 | $T_R$*; 4xSSC | $T_R$*; 4xSSC |

‡The hybrid length is that anticipated for the hybridized region(s) of the hybridizing polynucleotides. When hybridizing a polynucleotide to a target polynucleotide of unknown sequence, the hybrid length is assumed to be that of the hybridizing polynucleotide. When polynucleotides of known sequence are hybridized, the hybrid length can be determined by aligning the sequences of the polynucleotides and identifying the region or regions of optimal sequence complementarity.
†SSPE (1xSSPE is 0.15 M NaCl, 10 mM $NaH_2PO_4$, and 1.25 mM EDTA, pH 7.4) can be substituted for SSC (1xSSC is 0.15 M NaCl and 15 mM sodium citrate) in the hybridization and wash buffers; washes are performed for 15 minutes after hybridization is complete.
*$T_B$–$T_R$: The hybridization temperature for hybrids anticipated to be less than 50 base pairs in length should be 5–10° C. less than the melting temperature ($T_m$) of the hybrid, where $T_m$ is determined according to the following equations. For hybrids less than 18 base pairs in length, $T_m(° C.) = 2(\# \text{ of A + T bases}) + 4(\# \text{ of G + C bases})$. For hybrids between 18 and 49 base pairs in length, $T_m(° C.) = 81.5 + 16.6(\log_{10}[Na^+]) + 0.41(\% G + C) - (600/N)$, where N is the number of bases in the hybrid, and $[Na^+]$ is the concentration of sodium ions in the hybridization buffer ($[Na^+]$ for 1xSSC = 0.165 M).

It is clear to one skilled in the art that this hybridization step can be optimized using any suitable method of optimization that is established in the art of hybridization. These include, but are not limited to, techniques that increase the efficiency of annealing or hybridization from complex mixtures of polynucleotides (e.g., PERT; Miller, R. and Riblet, R., 1995. *Nucl. Acids Res.*, 23:2339–2340) or hybridization in different formats (e.g., using immobilized template or in microtiter well formats; Nikiforov, T. and Rogers, Y., 1995. *Anal. Biochem.*, 227:201–209).

Exploitation of an affinity moiety attached to the probe allows for the isolation of the probe-fragment hybrid. Probes can be designed to be of a specific sequence, and they can also be synthesized to contain a specific affinity moiety. Examples of such moieties are biotin and digoxygenin, which can be affinity separated along with the molecule to which each is attached, using avidin or anti-digoxygenin antibodies, respectively. The present invention describes methods for producing probe-fragment hybrids in which only such hybrids will contain an affinity moiety. The mixture of such hybrids and non-hybrid DNA fragments can be contacted with, for example, a solid support matrix that has that binding partner of the specific affinity moiety chemically attached. Conditions can be chosen such that binding occurs between the affinity moiety contained in the probe-fragment hybrid and the ligand that is chemically attached to the solid support matrix.

Solid-support matrices, e.g., agarose, cellulose, paramagnetic beads, fluorescently-labeled microbeads, coated plastic trays, coated chips and the like, are commercially available. Methods for attaching affinity moieties to such matrices, if not already available commercially, are known to those of skill in the art. Methods described herein allow for the concurrent use of multiple solid support matrices (e.g., paramagnetic and non-magnetic matrices, and fluorescently-labeled microbeads that havd different fluorescent labels and can be separated based on differences in fluorescence).

Upon washing, only probe-fragment hybrids containing the affinity moiety will remain, and the fragments that are a part of the hybrid will contain all or part of the target sequence. After washing and denaturation, single-stranded fragments are recovered. One of skill in the art will recognize that repetition of the binding, wash, and elution steps can increase the enrichment efficiency. Recovered fragments can be made double-stranded (by, for example, a primer extension reaction) or amplified (by, for example, PCR or ligation-mediated PCR) to produce an enriched pool of double-stranded DNA fragments. PCR and primer-extension methods are known to one of skill in the art.

The enriched sample of DNA fragments provides a suitable template for amplifying the target sequence of the fragments. High fidelity polymerase chain reaction ("hifiPCR") allows for accurate amplification of enriched DNA fragments. Additionally, primers for hifiPCR can be designed to contain a "clamp" (used herein to refer to a terminal high temperature iso-melting domain) that will be useful in subsequent CDCE steps. As used herein, hifiPCR refers to a polymerase chain reaction wherein the mutant fraction of each PCR-induced mutation is less than about $10^{-4}$. Preferably, the mutant fraction of each PCR-induced mutation is not greater than about $5 \times 10^{-5}$. HifiPCR of target regions can be carried out using, for example, Pfu polymerase where the amplification is limited to about six doublings. As described herein, the frequency of PCR-induced mutation at any base is dependent upon the number of PCR doublings and the error rate per base pair per doubling. Thus, suitable conditions for hifiPCR can be determined for any desired polymerase and target sequence.

The methods described herein are also applicable to isolating groups of fragments containing more than one sequence of interest utilizing probes attached to multiple solid supports (see Example 3). For example, more than one fragment containing a first target sequence can be enriched along with fragments containing a second target sequence. These enrichments can occur in the same step with different probes, or in parallel steps with different probes. Probes are designed in such a way as to allow for specific binding to a particular target sequence. Target sequences can be related (e.g., containing different coding regions for proteins involved in the same signaling pathway) or unrelated.

One of skill in the art will recognize that enriched pools of DNA fragments can be obtained from the total DNA fragment pool based on physical properties as well as sequence. For example, fragments of a particular size or mass can be enriched. Fragments can also be separated, for example, based on differences in melting temperature. Fragments that have unusually high or low melting temperatures can be enriched. Alternatively, a population of enriched DNA fragments can be obtained by first isolating RNA, and reverse-transcribing the sample to obtain cDNA fragments. Techniques for enrichment based on physical properties and for isolation and reverse transcription of RNA are known by on of ordinary skill in the art.

In Example 2, for example, fragments containing target sequences are enriched for mutant sequences before or after the affinity-based enrichment methods described herein. The further enrichment was facilitated by certain improvements in sample handling and loading. For example, approximately $2 \times 10^8$ total target copies enriched from MT1 genomic DNA were subjected to CDCE using a 540 µg ID capillary. Such a wide-bore capillary has a sufficient loading capacity (up to 5 µg DNA) permitting the separation of the heteroduplexes from the wild-type homoduplex in the presence of the residual cellular DNA and other impurities in the sample. Excellent CDCE resolution can be achieved in wide-bore capillaries at low electric field strengths to avoid the effect of Joule heating (Li, X.-C. and Thilly, W., 1996. *Electrophoresis*, 17:1884–1889). CDCE was performed at conditions for which all heteroduplexes co-eluted within a single fraction, well separated from the wild-type homoduplex fraction. The heteroduplex fraction was electroeluted as a fraction enriched in mutant sequences. The mutant enrichment efficiency was estimated based on the ratio of the total target copies loaded on the column to that eluted in the heteroduplex fraction. The enrichment was found to be 20-fold for the target-enriched cellular DNA samples, and over 200-fold for the CDCE-purified wild-type DNA sample.

One of skill in the art will recognize that either clamps or low temperature iso-melting domains can be added to DNA sequences (e.g., the at methods known in the art, e.g., PCR. Either or both of these iso-melting domains can be provided, for example, by a primer that includes a 5' 40 base sequence with a high or low melting temperature (e.g., a G/C rich sequence tend to have a higher melting temperature than an A/T rich sequence) and a 20 base target region specific sequence. The primer can be optionally detectably labeled. As used herein, a "label" is a distinguishing element such as, for example, a physical, chemical, or fluorescent modification. Suitable detectable labels include, for example, a radioisotope, an affinity label (e.g., biotin, avidin), a spin label, a fluorescent group (e.g., fluorescein) or a chemiluminescent group. In one embodiment, the primer is labeled at the 5' end with fluorescein.

Optionally, as a means to obtain a further mutant enrichment for the cellular DNA sample, CE can be performed at room temperature on the heteroduplex collection of the cellular DNA sample as described herein. This step separated true heteroduplexes from the residual wild-type sequences that migrated slower than the 271 bp wild-type homoduplex fragment. An additional 5- to 10-fold mutant enrichment was obtained by collecting the fraction containing the desired 271 bp APC fragment. Taken together, through the combination of CDCE and CE at room temperature, the mutants in the target-enriched cellular DNA were enriched 100–200-fold.

The mutant-enriched samples were next amplified by hifiPCR using native Pfu DNA polymerase and fluorescein-labeled primers to yield about $2.5 \times 10^{12}$ copies of the target sequence. Due to the pre-PCR mutant enrichment, the true cellular mutants at an initial fraction of $10^{-6}$ would have been present at $1-2 \times 10^{-4}$ in the PCR products. This can be compared with the expected fractions of PCR-introduced mutations. The Pfu DNA polymerase error rate has been reported to be around $10^{-6}$ errors per bp per doubling. The PCR-induced mutations after 21 doublings (from $10^6$ to $2.5 \times 10^{12}$ copies) would occur at a mutant fraction of $2 \times 10^{-5}$ per bp on average, or $2 \times 10^{-4}$ per bp for hotspots with a 10-fold increase in mutant fraction.

Figure 3:
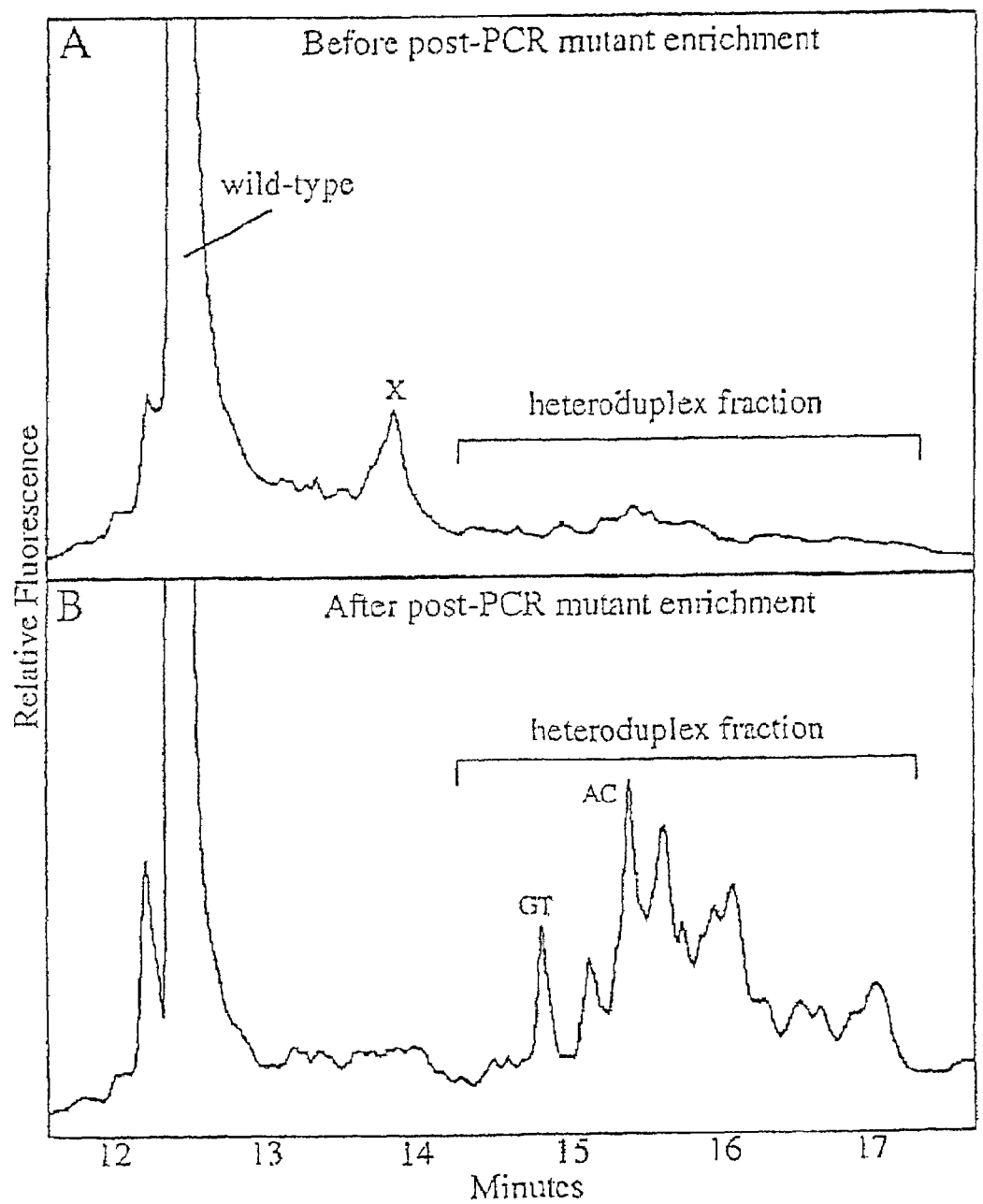
FIG. 3 is a graphical representation of post-PCR enrichment of mutant sequences by CDCE coupled with PCR. Depicted are CDCE separations of PCR products derived from the MNNG-treated MT1 cells. The horizontal axis represents the time when the peak reaches the detector since the beginning of the run. The vertical axis represents the relative intensity of fluorescence, which is proportional to the molecular number. The wild-type peak in both electropherograms is shown in 1/10 of its full height. (A) The mutant-enriched fraction from wide-bore CE separations was subjected to 40 cycles of hifiPCR. The PCR products were separated by CDCE and the heteroduplex fraction was collected. "X" marks a PCR byproduct. (B) The collected heteroduplex fraction was subjected to 38 cycles of PCR and separated by CDCE. "GT" and "AC" label the two heteroduplexes derived from the internal standard introduced at an initial mutant fraction of $10^{-5}$. The heteroduplex fraction was collected and amplified to further enrich the mutants.

The amplified PCR products were subjected to post-PCR mutant enrichment via CDCE in a regular 75 µm ID capillary (FIG. 3). The heteroduplex fraction was collected separately from the wild-type homoduplex (FIG. 3A), allowing about an additional 20-fold enrichment of mutants. The collected heteroduplexes were PCR amplified and run on a second CDCE. As shown in FIG. 3B, the two heteroduplex peaks of the internal standard at an initial mutant fraction of $10^{-5}$ were clearly identifiable at this stage, each constituting 2% of the wild-type peak. To observe mutants at lower mutant fractions, the heteroduplex collection was repeated to further enrich the mutants about an additional 5-fold.

The enriched pool of double-stranded DNA fragments contains multiple copies of a particular fragment of interest. The particular fragment can be, for example, one that contains a specific coding sequence, where the sequence of each of the fragments in the pool is similar, but, since the original DNA sample was obtained from multiple cells from one or more individuals in a population, the fragments will exhibit small sequence variations (polymorphisms) at particular polymorphic sites. A particular polymorphic variant is referred to herein as an "allele." The most common allele, or the one that leads to a normal phenotype, is referred to herein as the "wild-type" allele, and it is distinguished from other variants referred to herein as "mutant" alleles. Thus, even though the enriched pool of DNA fragments contains similar molecules, several alleles can be represented at one or more polymorphic sites on different fragments. The frequency, by definition, of the wild-type allele at any given polymorphic site is the highest, and some of the mutant alleles might be, in fact, quite rare in the pool. Detection of mutant vs. non-mutant (e.g., wild-type) alleles in the pool of enriched DNA fragments requires a method of separating such alleles.

Figure 4A:
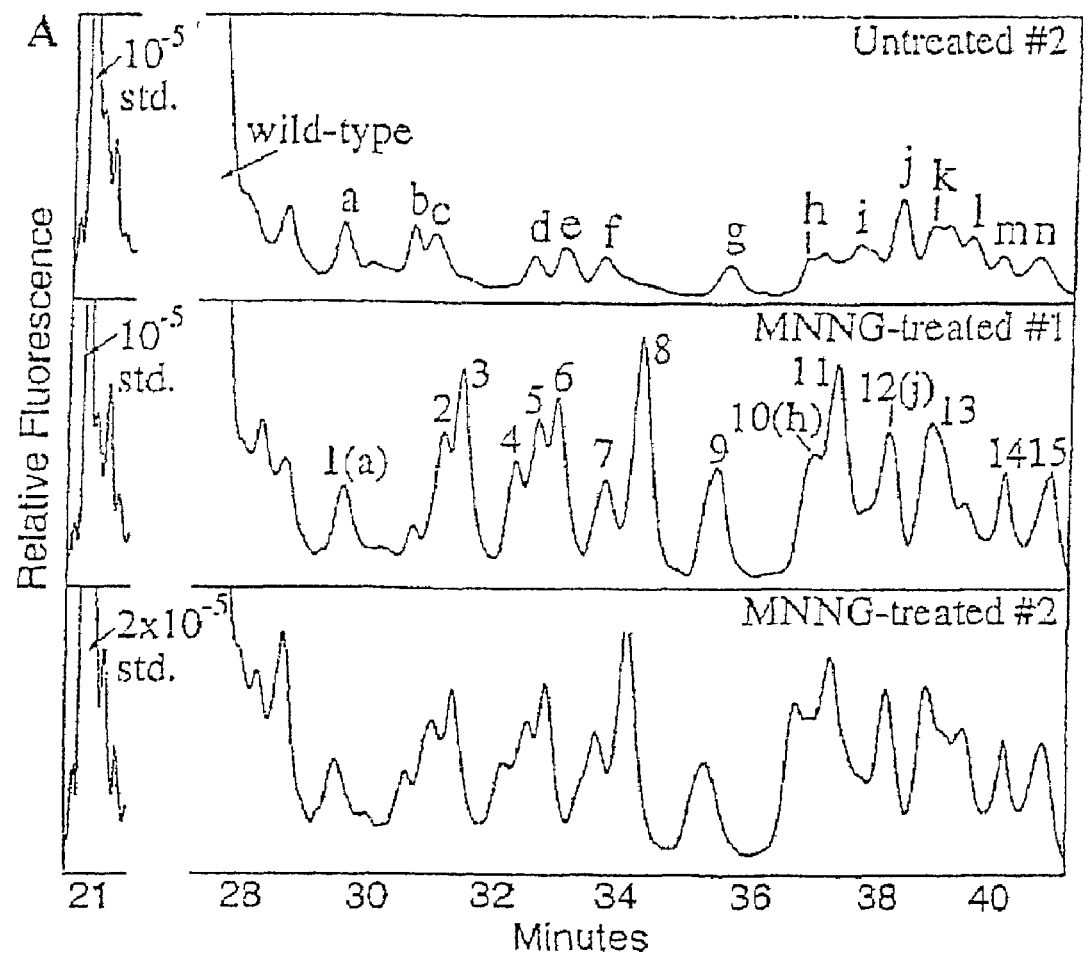
FIGS. 4A and 4B are graphical representations of CDCE separations of mutant homoduplexes derived from two MNNG-treated and two untreated MT1 cultures and the CDCE-purified wild-type DNA. The axes are as in FIG. 3. (A) Comparison of mutants derived from two MNNG-treated and one untreated samples. The wild-type peak and the internal standard (std) at its initial mutant fraction are indicated. The standard (std) peak is shown in ½ of its height in "Untreated #2" and "MNNG-treated #1" samples, and ¼ of its height in "MNNG-treated #2". (B) Comparison of mutants derived from the CDCE-purified wild-type DNA (Pfu-PCR noise control) and two untreated samples. Each mutant peak that has been isolated and sequenced is designated by a letter or number. "SS" marks single-strand DNA.
Figure 4B:
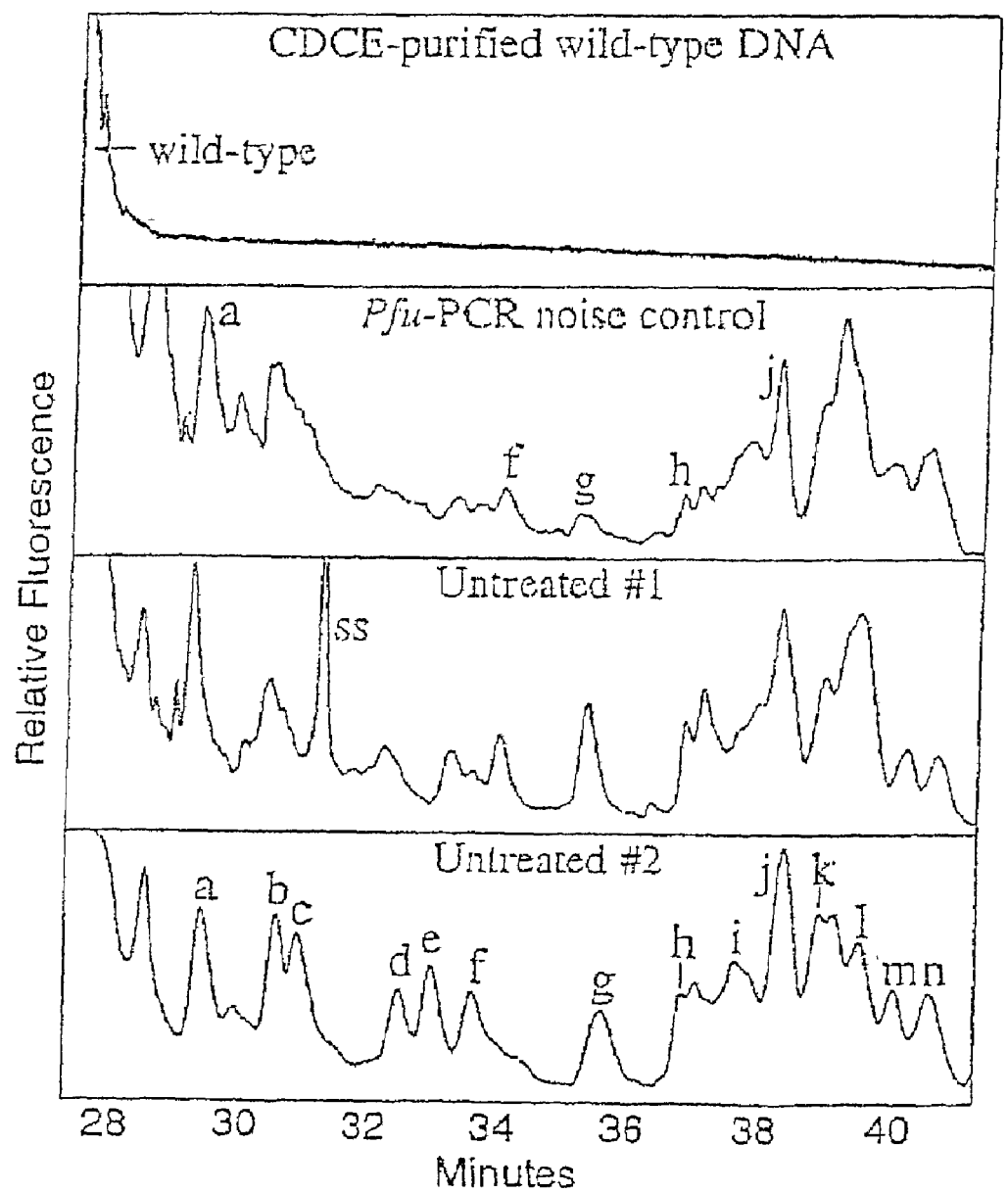

Shown in FIG. 4 are the final CDCE separations of mutant homoduplexes derived from two MNNG-treated and two untreated MT1 cultures, as well as the CDCE-purified wild-type DNA serving as a PCR noise control (see Example 2). Compared to the purified wild-type DNA and untreated samples, both MNNG-treated samples contained a distinct set of peaks, nearly all of which migrated after the wild-type peak (FIG. 4A), indicating that they were mutant homoduplex sequences with melting temperatures ($T_m$) lower than the wild-type homoduplex. As no strong mutant peaks appeared with melting temperatures higher than the wild-type, the analysis focused on the low $T_m$ mutants.

Each mutant peak identified was designated by a letter in the untreated sample or a number in the MNNG-treated sample (FIG. 4A). The migration times and mutant fractions of each set of peaks in the replicate experiments exhibited excellent reproducibility when CDCE was run at several different water jacket temperatures. Although co-migration on CDCE is not sufficient proof of identity, in previous studies, over 90% of the peaks identified by co-migration with mutant standards were indeed verified by either direct sequencing or on-column hybridization. As described in Example 2, several mutant peaks derived from the CDCE-purified wild-type DNA sample (FIG. 4B) were confirmed to be identical to their co-migrating counterparts in the untreated MT1 samples by direct sequencing.

Figure 5:
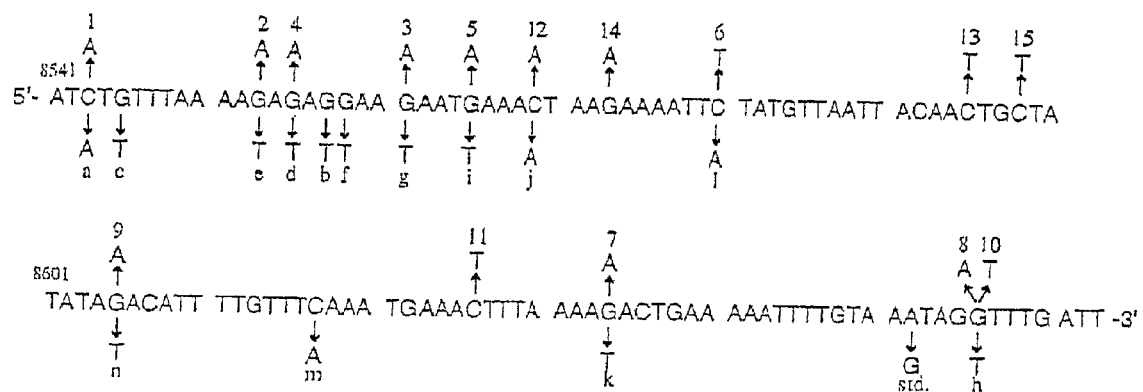
FIG. 5 is a detailed view of the APC gene fragment (SEQ ID NO.: 5) showing the distribution of base substitutions in the APC gene target sequence (APC cDNA bp 8543–8663) in MNNG-treated and untreated MT1 cells. Mutants from the treated cells are shown above the wild-type sequence, while those from the untreated are below the sequence. Mutant labels correspond to those in FIG. 4. The base substitution of the internal standard (std) is also indicated.
Figure 6:
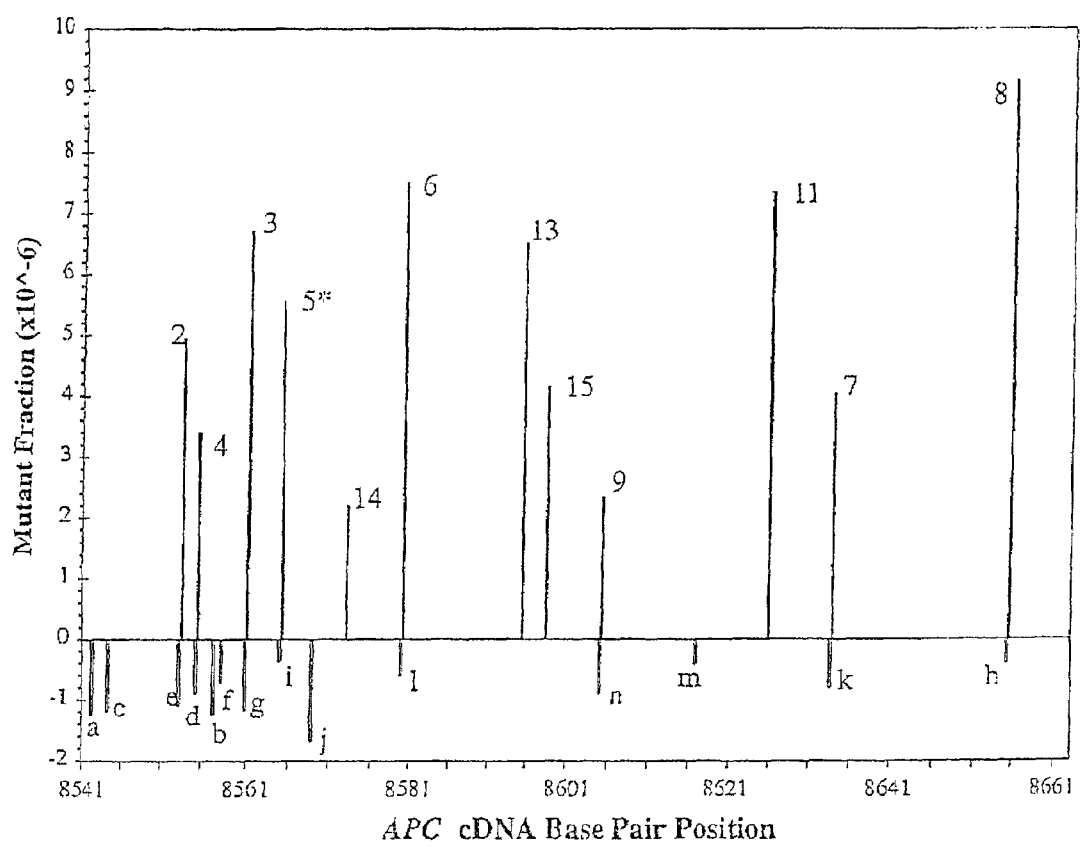
FIG. 6 is a graphical representation of MNNG-induced and background point mutational spectra in the APC gene target sequence in MT1 cells. The horizontal axis represents the APC cDNA bp position of the target sequence. The height of each vertical bar represents the average fraction of each mutant in the replicate samples. Each mutant is labeled with a number or letter corresponding to that in FIGS. 4 and 5. Open bars represent background GC->TA transversions; filled bars represent MNNG-induced GC->AT transitions. Except for peak 5 (indicated by "*"), all transitions occurred at guanine residues preceded (5') by a purine. The mutant fraction was measured by comparing the area under each mutant peak with that under the internal standard in a CDCE electropherogram. To obtain an accurate measurement, CDCE was performed at different water-bath temperatures (between 64.8° C. and 65.5° C.). For each peak to be measured, the appropriate electropherogram showing the best separation of this peak from its adjacent ones was chosen.

FIG. 5 shows the position, type of mutation and sequence context for all of the mutants identified in MNNG-treated and untreated samples (see Example 2). Each of the fourteen mutants found in the untreated samples contain a GC->TA transversion. Their mutant fractions range from $4 \times 10^{-7}$ to $1.8 \times 10^{-6}$ as determined by comparison to the internal standard (FIG. 6). In contrast, twelve out of the fifteen mutants in the MNNG-treated samples contained a GC->AT transition at a mutant fraction between $2.2 \times 10^{-6}$ and $9.2 \times 10^{-6}$ (FIG. 6). The three exceptions (peaks 1, 10, and 12) were found to be identical to three mutants in the untreated sample (peaks a, h and j, respectively), suggesting that they belong to the set of background mutations.

The observation of the twelve GC->AT transitions in the MNNG-treated MT1 cultures is consistent with the predicted mis-coding potential of $O_6$-methylguanine which is proposed to be the major pre-mutagenic lesion produced by MNNG. An analysis of the influence of the neighboring base sequences on MNNG-induced mutation is shown in Table 2, which includes all of the 29 guanine sites in the APC target sequence. On average, a guanine residue preceded 5' by a purine is seven times more likely to be mutated than one preceded 5' by a pyrimidine. In addition, the 3' flanking base also seems to exert a slight influence on mutation in favor of GPu 3' sites. As shown in Table 2, the average frequency of MNNG-induced GC->AT transitions appears to decrease in the order of 5' PuGPu 3'>5' PuGPy 3'>5' PyGPu 3'>5' PyGPy 3'.

TABLE 2

Influence of the 5' and 3' flanking bases on MNNG-induced GC → AT transitions

| Sequence (5' → 3') | # guanine sites | # mutated sites | Total mutant fraction (×10⁶) | Average mutant fraction per site (×10⁶) |
|---|---|---|---|---|
| PuG | 17 | 11 | 59 | 3.5 |
| PyG | 12 | 1 | 6 | 0.5 |
| GPu | 15 | 8 | 37 | 2.5 |
| GPy | 14 | 4 | 27 | 1.9 |
| PuGPu | 10 | 7 | 47 | 4.7 |
| PuGPy | 7 | 4 | 18 | 2.6 |
| PyGPu | 5 | 1 | 6 | 1.2 |
| PyGPu | 7 | 0 | 0 | 0 |

As a result of the invention described herein, methods are now available to measure point mutational spectra of nuclear single-copy genes without phenotypic selection. Mutational spectrometry of nuclear genes, exemplified here by a 121 bp APC gene sequence, has been examined. First, sequence-specific hybridization coupled with a biotin-streptavidin capture system was employed to enrich the target sequence from genomic DNA by about $10^4$-fold. Using this strategy, several milligrams of genomic DNA, which are required for reproducible observations of nuclear gene mutations at mutant fractions as low as $10^{-6}$, were reduced to less than 1 μg containing over 70% of the desired target sequence. This large reduction in sample size permitted the subsequent mutational analysis. Furthermore, this method of enriching was applied to four other nuclear sequences located in the human p53, $K_1$-ras and HPRT genes from the same genomic DNA samples for mutational analysis.

Another technical aspect involved the use of wide-bore capillary electrophoresis to enrich for mutant sequences in the presence of the residual 1 μg of cellular DNA. Compared to the CDGE technique used in earlier studies, CDCE using a 540 μm ID column provided a large sample loading capacity without compromising resolution or target sequence yield (almost 100%). A >100-fold mutant enrichment was achieved through two consecutive separations of CDCE and CE at room temperature. The high efficiency of mutant enrichment using CDCE (both wide-bore for enrichment prior to PCR and regular CDCE to obtain mutational spectra) and high fidelity PCR (hifiPCR) using Pfu DNA polymerase (U.S. Pat. No. 5,976,842, the entire teachings of which are incorporated herein by reference) to separate mutant from non-mutant fragments (for details of CDCE and hifiPCR, see, for example, Khrapko, K. et al., 1997. *Nucl. Acids Res.*, 25:685–693; the entire teachings of which are incorporated herein by reference), created a means to measure nuclear point mutations at frequencies at or above $10^{-6}$.

The approach described herein is generally applicable to any 100 bp iso-melting DNA sequences juxtaposed to a naturally occurring high $T_m$ domain. Such a juxtaposition renders such sequences suitable for CDCE analysis. While nearly all genes contain such sequences, they represent about 9% of the sequences in several human genes for which full length genomic sequences are available. Nevertheless, this general approach can be extended to 98% of the remaining gene sequences by attachment of an artificial GC clamp.

It is also recognized by one of skill in the art that mutations, nuclear, mitochondrial, or otherwise, can be detected in an enriched pool of DNA molecules by other methods of mutational analysis such as, for example, DGGE, CDGE, allele-specific PCR, and the like.

The invention will be further described with reference to the following non-limiting examples. The teachings of all the patents, patent applications and all other publications and websites cited herein are incorporated by reference in their entirety.

EXAMPLES

Example 1

Analysis of Mutations Using Affinity Enrichment and CDCE

Constant denaturant capillary electrophoresis (CDCE) separates macromolecules based on differences in their melting temperatures. Specific apparatus and operating conditions have been described previously that allow CDCE to separate point mutants among 100 to 150 bp iso-melting DNA sequences. CDCE coupled with high-fidelity DNA polymerase chain reaction (hifiPCR) has been applied to the measurement of point mutational spectra in human cell and tissue samples.

Figure 1:
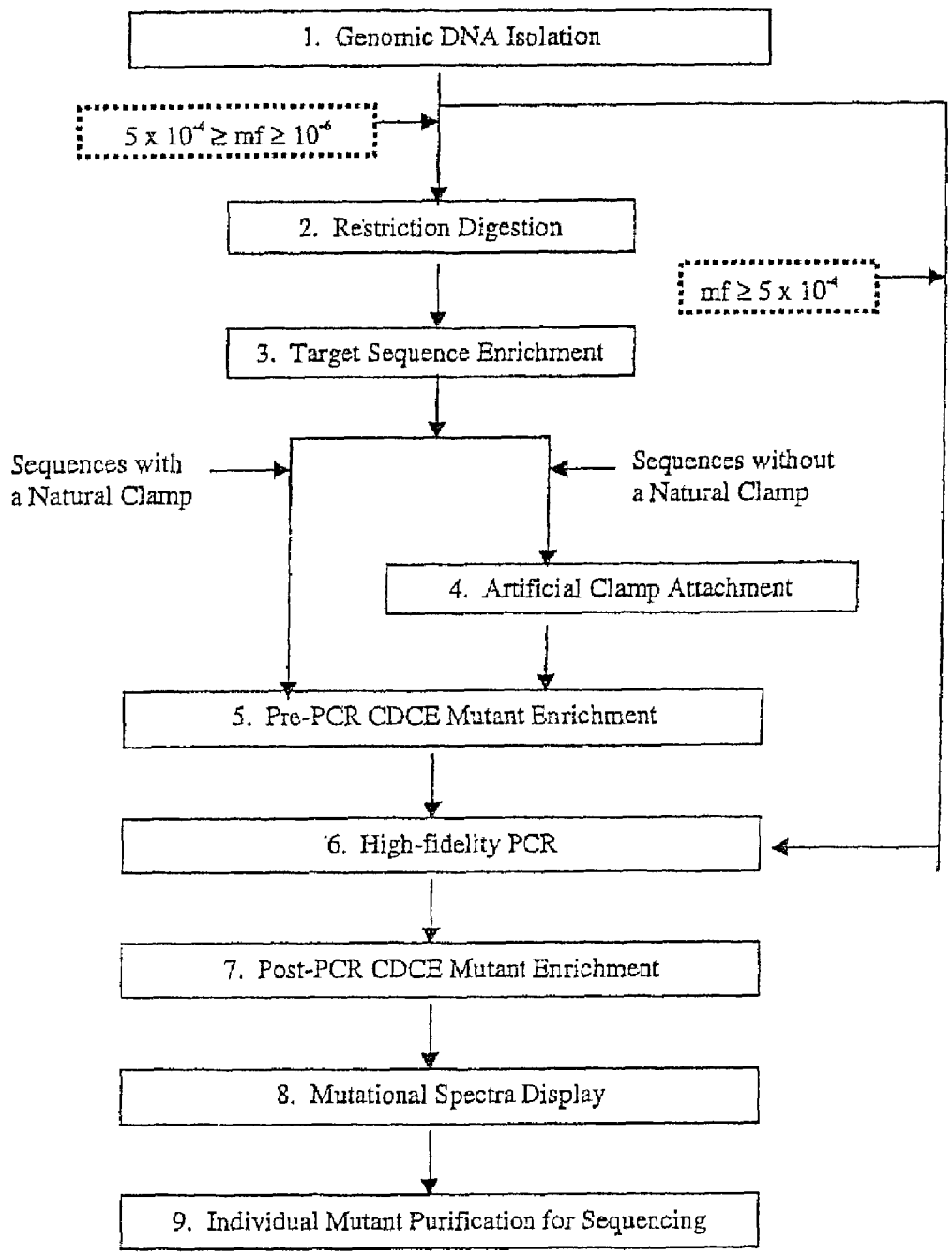
FIG. 1 is a diagram depicting the sample handling steps necessary to detect mutations at different fraction levels. For mutation detection at fractions as low as 10–6, include steps 1–3 and 5 prior to performance of steps 6–9.

The specific protocol for measuring point mutations depends on the desired degree of sensitivity as outlined in FIG. 1. To detect mutant fractions (mf) down to $5 \times 10^{-4}$, one isolates genomic DNA (FIG. 1, with a high-fidelity DNA polymerase (FIG. 1, step 6) and enriches mutant sequences relative to the wild-type sequences (FIG. 1, step 7). Mutants in the enriched mixture are then separated from each other and measured by CDCE (FIG. 1, step 8). At this stage, the individual mutants are purified and sequenced for their identification (FIG. 1, step 9). This method has found three important applications: detection of point mutations in phenotypically altered human cells after chemical treatment, detection of cancer cells in normal tissues, and identification of single-nucleotide polymorphisms (SNPs) in pooled human blood samples.

The analysis of point mutations at fractions down to $10^{-6}$ requires three additional steps prior to hifiPCR (FIG. 1, step 6). These steps are: liberation of a desired sequence from genomic DNA by restriction digestion (FIG. 1, step 2), enrichment of the desired sequence from restriction-digested DNA (FIG. 1, step 3) and pre-PCR mutant enrichment by CDCE (FIG. 1, step 5). Even Pfu DNA polymerase, the highest fidelity DNA polymerase available, creates mutations at a rate that interferes with the initial mutant fractions of approx $5 \times 10^{-4}$. Thus, the pre-PCR mutant enrichment is essential for detecting low fraction mutations as low as $10^{-6}$. The sensitivity of this method has been demonstrated in chemically-treated human cells without reference to phenotypic selection.

The development of the mutation detection methods is outlined in FIG. 1. A part of the human adenomatous polyposis coli (APC) gene (APC cDNA—by 8543–8683) is used as a target sequence. This APC sequence contains an iso-melting DNA domain juxtaposed to a domain of a higher melting temperature (APC cDNA—by 8441–8542). This higher melting region works as a "clamp" that allows the separation of point mutations in the target domain from the wild-type under appropriate denaturing conditions. Approximately 9% of the human genome is comprised of 100 bp sequence elements with such a natural neighboring clamp.

If a sequence of interest does not have a natural clamp, an artificially-created clamp can be attached by, for example, PCR to detect point mutations at fractions down to $5 \times 10^{-4}$. However, a PCR-based clamp attachment method will also allow the introduction of polymerase-created mutations, which will prevent mutation detection at fractions below $5 \times 10^{-4}$ level.

Materials

Isolation of Genomic DNA

Genomic DNA can be isolated from, for example, blood or solid tissues. Materials 1–4 are necessary for the tissue samples, and steps 5 and 6 are needed for the blood samples.
1. Dimethyl sulfoxide (DMSO)
2. Surgical scalpels.
3. Liquid nitrogen.
4. Mortar and pestle.
5. ACD Solution B: 0.48% citric acid, 1.32% sodium citrate, 1.47% glucose.
6. Phosphate-buffered saline (PBS): dissolve 8 g of NaCl, 0.2 g of KCl, 1.44 g of $Na_2HPO_4$, and 0.24 g of $KH_2PO_4$ in 800 mL of deionized $H_2O$ ($dH_2O$). Adjust the pH to 7.4 with HCl and add $dH_2O$ to 1L.
7. 10×TE buffer: 50 mM Tris-HCl, pH 8.0, 10 mM EDTA
8. Proteinase K (Boehringer Mannheim, Indianapolis, Ind.). Make a fresh solution of proteinase K in $dH_2O$ at 20 mg/mL on the day of DNA isolation. To limit autodigestion, store at $-20°$ C. until ready to use.
9. 10% Sodium dodecyl sulfate (SDS): dissolve 100 g of SDS in 900 mL of $dH_2O$ (heat to 68° C. to assist dissolution). Adjust the pH to 7.2 with HCl and add $dH_2O$ to 1L.
10. 10 mg/mL RNaseA (Boehringer Mannheim). Store at $-20°$ C.
11. 5 M NaCl: dissolve 292.2 g of NaCl in 800 mL of $dH_2O$ and add $dH_2O$ to 1L.
12. 100% Ethanol. Chill to $-20°$ C. before using.
13. 70% Ethanol. Chill to $-20°$ C. before using.

Restriction Digestion and Internal Standard Introduction.
1. Restriction endonucleases: HaeIII and XbaI (New England Biolabs, Beverly, Mass.). Store at $-20°$ C.
2. 10×NEBuffer #2: 10 mM Tris-HCl, pH 7.9 at 25° C., 10 mM $MgCl_2$, 50 mM NaCl, 1 mM dithiothreitol (DTT). Store at $-20°$ C.
3. Items required for PCR and CDCE.
4. Primers for a mutant internal standard construction (polyacrylamide gel electrophoresis [PAGE] purified). Primers for the target APC sequence are as follows: primer 1: 5'-CCA TCT CAG ATC CCA AC<u>T</u>CC-3' (APC cDNA bp 8422–8441; SEQ ID NO.: 6; the fluorescein-labeled thymine underlined), primer 2: 5'-AAC AAA AAC CCT CTA ACA AGA ATC AAA CCT A<u>C</u>T TAC-3' (complementary to APC cDNA bp 8648–8683; SEQ ID NO.: 7; underlined C forms an A:C mismatch at bp 8562) and primer 3: 5'-TAT AAT CTA GAA ATG ATT GA-3' (complementary to APC cDNA bp 8894–8913; SEQ ID NO.: 8). Dilute each primer with $dH_2O$ to a concentration of $1.2 \times 10^{13}$ molecules μL and store at $-20°$ C.

Measurement of Point Mutational Spectra
5. Prepare a 2×PCR master mix #1 with primers 1 and 2; 2×PCR master mix #2 with primers 1 and 3.

Target Sequence Enrichment
1. Two oligonucleotide probes are complementary to the Watson and Crick strands of the target sequence. The probes must meet the three following requirements: biotinylated at the 5' end through a 12–18 carbon spacer arm, purified by high-performance liquid chromatography (HPLC) or PAGE, and have similar melting temperatures.

Probes for the target APC sequence are BP1: 5'-CAA AAC TGA CAG CAC AGA ATC CAG TGG AAC-3' (APC cDNA bp 8472–8501; SEQ ID NO.: 1) and BP2: 5'-AAG ACC CAG AAT GGC GCT TAG GAC TTT GGG-3' (complementary to APC cDNA bp 8501–8530; SEQ ID NO.: 2). Dilute each probe with dH$_2$O to a concentration of $1.2 \times 10^{13}$ molecules/μL and store at $-20°$ C.
2. 20×SSPE: dissolve 17.53 g of NaCl, 2.76 g of NaH$_2$PO$_4$.H$_2$O and 0.74 g of EDTA in 90 mL of dH$_2$O. Adjust the pH to 7.4 with NaOH and add dH$_2$O to 100 mL.
3. 10 mg/mL streptavidin-coated paramagnetic beads (MPG®; CPG, Lincoln Park, N.J.). Pre-wash with the washing buffer (step 5) before using.
4. Neodymium magnet.
5. Washing buffer: 1 M NaCl, 10 mM Tris-HCl, pH 7.6, 2 mM EDTA.
6. 10× reannealing buffer: 2 M NaCl, 100 mM Tris-HCl, pH 7.6, 20 mM EDTA.
7. 0.025 μm membrane filters (Millipore, Marlborough, Mass).

Pre-PCR Mutant Enrichment
1. Restriction endonucleases: AccI and Sau3AI. Store at $-20°$ C.
2. 10×NEBuffer #4: 20 mM Tris-acetate, pH 7.9 at 25° C., 10 mM magnesium acetate, 50 mM potassium acetate, 1 mM DTT. Store at $-20°$ C.
3. 100× bovine serum albumin (BSA): 10 mg/mL BSA. Store at $-20°$ C.
4. Dialysis buffer: 0.1×TBE (dilute from 5×); 5×TBE: dissolve 54 g Tris-base, 27.5 g boric acid, 10 mL 0.5 M EDTA pH 8.0, in 1 liter of dH$_2$O.
5. Items required for CDCE.
6. 542 μm inner diameter (id) and 665 μm outer diameter (od) fused-silica capillaries (Polymicro Technologies, Phoenix, Ariz.). The DNA loading capacity of 540 μm id capillaries is approx 10 μg.
7. Stainless steel tubing (6 cm or longer, 0.042" id, 0.027" od and 19 in. gauge) (Small Parts Inc., Miami, Fla.).
8. 0.5 mm id and 1.5 mm od. Teflon tubing (Varian Associates, Inc., Walnut Creek, Calif.).
9. 0.8× "TBEB" elution buffer: 0.8×TBE, 0.24 mg/mL BSA. Additional dilutions are 0.4×TBEB and 0.1×TBEB. Store at $-20°$ C.

High-Fidelity PCR
1. Primers for the target APC sequence with a natural clamp are: AP1: 5'FITC-GAA TAA CAA CAC AAA GAA GC-3' (APC cDNA bp 8441–8460; SEQ ID NO.: 3) and AP4H: 5'-AAC AAA AAC CCT CTA ACA AG-3' (complementary to APC cDNA bp 8664–8683; SEQ ID NO.: 4). Primer 4 is replaced with clamp 1 for the same target sequence attached to an artificial clamp. One primer is fluorescein-labeled at the 5' end (5' FITC; primer 4 or clamp 1, the primer in the clamp region). Dilute each primer with dH$_2$O to a concentration of $1.2 \times 10^{13}$ molecules/μL and store at $-20°$ C.
2. dNTP mix: 25 mM mixture of four dNTPs (Pharmacia, Piscataway, N.J.) dATP, dCTP, dGTP, and dTTP-each 100 mM in equal volume and store at $-20°$ C.
3. Native Pfu DNA polymerase (2.5 U/μL) (Stratagene. La Jolla, Calif.). Store at $-20°$ C.
4. 10× reaction buffer for native Pfu DNA polymerase: 200 mM Tris-HCl, pH 8.0, 20 mM MgCl$_2$, 100 mM KCl, 60 mM (NH$_4$)$_2$SO$_4$, 1% Triton X-100, 100 μg/mL nuclease-free BSA (Stratagene, La Jolla, Calif.). Store at $-20°$ C.
5. 2×PCR master mix with primers 4 and 5 (step 1): 100 μL of 2× master mix contains 20 μL 10× native Pfu DNA polymerase reaction buffer, 2.0 μL each primer ($1.2 \times 10^3$ molecules/NL), 0.8 μL of 25 mM dNTPs, 2.0 μL of 100 ×BSA and 73.2 μL of dH$_2$O. Store the mixture at $-20°$ C.
6. 10 and 50 μL glass capillary tubes (Idaho Technology, Idaho Falls, Id.).
7. Air Thermo-Cycler (Idaho Technology, Idaho Falls, Id.).
8. Glass cutter
9. To perform post-PCR mutant enrichment, mutational spectra display and individual mutant purification, see the materials required for both PCR and for CDCE.

Methods
1. To minimize potential contamination of samples by artificially-created or PCR-generated DNA mutants, the procedures performed before hifiPCR must be carried out in a separate isolation laboratory equipped with high-throughput HEPA air filters.
2. No PCR products can be permitted in such a laboratory except for very diluted mutant internal standard stocks ($<10^3$ copies/μL).

Genomic DNA Isolation
1. For tissue samples: cut a tissue sample (stored in 20% DMSO at $-70°$ C. or $-20°$ C.) into small pieces with a scalpel. Deep-freeze the pieces of the tissue in liquid nitrogen and grind them into a fine powder using a mortar and pestle. Place the powdered tissue in a centrifuge tube and resuspend it in 1 mL of 1×TE buffer per 50 mg of tissue. Proceed to step 3.
2. For blood samples: add 1 volume of PBS to a blood sample (stored in ACD solution B (1 mL ACD solution B/6 mL of blood) at $-70°$ C. or $-20°$ C.) and after mixing, centrifuge at 3500 g for 15 minutes. Carefully discard as much of the supernatant as possible without disturbing the pellet at the bottom of the tube. Suspend the pellet in 1 mL of 1×TE buffer for each 3 mL of blood.

Measurement of Point Mutational Spectra
3. Add 20 mg/mL of proteinase K and 10% SDS to the final concentrations of 1 mg/mL and 0.5%, respectively. Incubate the solution while continuously mixing the contents thoroughly in a water-bath shaker (100–200 rpm) at 50° C. for 3 hours.
4. Add 10 mg/mL RNaseA to a final concentration of 20 μg/mL. Incubate the suspension in a water-bath shaker and mix thoroughly (100–200 rpm) at 50° C. for 1 hour.
5. Centrifuge at 10,000 g for 15 minutes while keeping the centrifuge temperature at 4° C. Transfer the central portion of the supernatant into a new tube by careful pipeting. Repeat this step two or three times and combine all of the transferred supernatant.
6. Add 5 M NaCl to the transferred supernatant tube to a final concentration of 250 mM and add two volumes of chilled 100% ethanol. Mix by inverting the tube gently several times (a DNA spool should start to form upon mixing).
7. Transfer the DNA spool into a microcentrifuge tube and wash with 1 mL of chilled 70% ethanol. Repeat this washing and discard as much of 70% ethanol as possible.
8. Air-dry the DNA spool by leaving it in the tube with the cap open at room temperature for approx 30 minutes. Add 0.1×TE buffer to a DNA concentration of 2–4 mg/mL. Pipet the DNA sample mixture up and down several times upon dissolving the spool at room temperature for complete mixing.

9. Add 5 μL of the DNA sample mixture into 0.5 mL of dH$_2$O and measure A$_{260}$ and A$_{280}$. A typical DNA yield and ratio of A$_{260}$ to A$_{280}$ are over 90% and 1.4–1.6, respectively with the DNA suitable for both restriction digestion and PCR amplification.

Restriction Digestion and Internal Standard Introduction

Restriction Digestion

1. Add 10×NE #2 to a final concentration of 1× and HaeIII and XbaI to an enzyme/DNA ratio of 1 U/μg to the DNA sample with a DNA concentration of 2–3 mg/mL.
2. Mix thoroughly and incubate at 37° C. overnight.

Internal Standard Preparation

1. A 492 bp artificial mutant (APC cDNA-bp 8422–8913) with an AT->GC transition at APC cDNA bp 8652 is constructed to serve as an internal standard. This internal standard mutant is compatible with the 482 bp APC fragment liberated from genomic DNA by HaeIII and XbaI.
2. Add 1 μL of the restriction digested DNA sample into 9 μL of dH$_2$O (10-fold dilution).
3. Preparation of a 262 bp APC mutant fragment (APC cDNA bp 8422–8683): mix 1 μL of the diluted sample with 5 μL of 2×PCR master mix # 1, 3.6 μL of dH$_2$O and 0.4 μL of Pfu DNA polymerase. Amplify the fragment.
4. Preparation of a 492 bp APC wild-type fragment (APC cDNA bp 8422–8913): amplify the fragment as described in step 3 except use 2×PCR master mix #2.
5. The preparation of a 492 bp APC mutant fragment (internal standard) mixture: mix together 1 μL of the PCR product from step 3, 1 μL of the PCR product from step 4 (diluted 10-fold in dH$_2$O), 5 μL of 2×PCR master mix #2, 2.6 μL of dH$_2$O, and 0.4 μL of Pfu DNA polymerase. Amplify the fragment with an appropriate number of cycles to convert all the primers into product.
6. Make subsequent stock dilutions of the amplified mutant internal standard (492 bp) with dH$_2$O, 10-fold each time at concentrations down to 10$^2$ copies/μL.

Internal Standard Introduction

1. Mix together, 1 μL of the 10-fold diluted restriction digested DNA sample, 1 μL of the internal standard stock of 10$^4$ copies/μL, 5 μL of 2×PCR master mix, 2.6 μL of dH$_2$O , and 0.4 μL Pfu DNA polymerase. Amplify the target sequence.
2. Separate the PCR product by CDCE and measure the copy number of the target sequence in the restriction digested DNA sample. The target sequence copy number can be quantified by measuring the areas under the separated peaks, which represent wild-type homoduplex ($A_w$), mutant homoduplex ($A_m$), and wild-type/mutant heteroduplexes ($A_h$). The equation to be used for the quantification is as follows:

$$([A_W+A_h/2]/[A_m+A_h/2])\times 10\times \text{copies}/NL)\times df = \text{\# of target sequence copies}/\mu L,$$

in which 10× copies/μL, is the concentration of the internal standard stock used for PCR (10$^4$/μL), and df is a dilution fold of the original sample (10-fold).

3. Add the internal standard at a desired fraction to the restriction digested DNA sample.

Target Sequence Enrichment

1. Add each probe 1 and probe 2 to a probe/target sequence molar ratio of 5×10$^4$ to the restriction enzyme digested sample (with added internal standard), and 20×SSPE to a final concentration of 6×. Mix thoroughly and distribute into several 1.5-mL microcentrifuge tubes (~0.5 mL/tube).
2. Place the sample tubes containing the mixture in a boiling water bath for 2 minutes, followed by immediate chilling in an ice bath for 10 minutes. Incubate the chilled sample in a thermomixer at 58° C. for 2 hours. This is the probe-target hybridization temperature for the target APC sequence.
3. Add 0.4 mg of MPG beads/10$^8$ copies of the target sequence and incubate the suspension in a rotating thermomixer (1000 rpm) at 50° C. for 1 hour. Gather the beads to the side of each sample tube by placing a magnet against the wall of the tube. Remove the solution and combine all the beads into one tube.
4. Resuspend the beads in the washing buffer at a concentration of 10 mg/mL and incubate in a rotating thermomixer (1000 rpm) at 50° C. for 5 minutes. Remove the buffer and retain the beads. Repeat this washing step three times.
5. Elute the target sequence from the beads. Incubate the beads at 20 mg/mL in dH$_2$O for 2 minutes at 70° C. Magnetically separate the eluate from the beads and transfer the eluate into a fresh tube. Repeat this step one more time and combine the eluates.
6. Reduce the volume of the eluate to about 10 μL by speed-vac.
7. Add the 10× reannealing buffer to the reduced-volume eluate to a final concentration of 1× and incubate at 55° C. for 16 hours. During incubation, the wild-type/mutant heteroduplex DNA fragments are formed.
8. Desalt the reannealed sample by drop dialysis: float a 0.025 μm membrane filter on the surface of 0.1×TE buffer in a container (e.g., a plastic Petri dish) and place the container on a stir plate. Transfer the sample on the floating membrane filter by pipeting. Dialyze the sample on the membrane filter with 0.1×TE buffer by stirring the buffer with a stir bar for 2 hours.
9. Reduce the volume of the desalted sample to approx 10 μL by speed-vac.
10. The procedures described in this subsection allow the enrichment of a desired target relative to non-target fragments in a pool of genomic DNA restriction fragments. Although the values may vary for different targets, a typical enrichment (fold) and yield for the target APC sequence are about 10$^4$ and 70%, respectively. Thus, this procedure can reduce the DNA sample size of 600 μg to 60 ng where over 10$^8$ copies of the target sequence are present. The reduced sample volume is suitable for both pre PCR mutant enrichment and clamp attachment.

Pre-PCR Mutant Enrichment

1. To the target sequence-enriched sample, add both 10×NEBuffer #4 and 100×BSA to a final concentration of 1×. Add 5 U of AccI and Sau3AI and mix thoroughly. Incubate at 37° C. for 16 hours and proceed to step 3.
2. Desalt the restriction digested sample by drop dialysis with 0.1×TBE.
3. Reduce the volume of the sample to approx 4 μL by speed-vac.
4. Prepare a 20 cm-long coated capillary of 540 μm id with a detection window 7 cm away from the anodic end. The detection window can be made by peeling off approx 0.5 cm of the outer surface of the capillary. Place the prepared capillary on a CDCE instrument and insert a portion of the capillary (near the cathodic end) in a water jacket (equipped with stainless steel tubing to hold the capillary) that is connected to a constant temperature circulator.

5. Set the circulator to the optimal temperature for the separation of mutant/wild-type heteroduplexes from wild-type homoduplexes.

6. Replace the 5% linear polyacrylamide matrix (about 35 µL) within the capillary.

7. Transfer 4 µL of the sample (step 3) by pipet into a piece of Teflon tube (1 cm long and 0.5 mm id). Remove the buffer reservoir away from the cathodic end of the capillary and mount the Teflon tube onto the capillary end. Bring the buffer reservoir to the end of the Teflon tube and electrokinetically inject the sample at 80 µA for 2 minutes. Remove the Teflon tube from the capillary end and perform electrophoresis at 80 µA.

8. Stop electrophoresis just before mutant heteroduplexes start to reach the anodic end of the capillary and remove the buffer reservoir from the capillary end. Place a platinum wire into 10 µL of 0.8×TBEB elution buffer in a 0.5-mL microcentrifuge tube and simultaneously dip the anodic end of the capillary in the tube. Electroelute mutant heteroduplex at 80 µA into the elution buffer for 15–20 minutes.

9. Dialyze the eluted sample by drop dialysis with 0.1×TBE.

10. Reduce the volume of the sample to approx 4 µL by speed-vac.

11. Remove the water jacket from the capillary and replace the matrix inside the capillary (see step 5).

12. Electroinject the sample into the capillary (see step 6) and perform electrophoresis at 80 µA and at room temperature (RTCE).

13. Stop electrophoresis just before the target sequence in double-strand form to reach the anodic end of the capillary. Electroelute the target sequence at 80 µA in 10 µL of 0.4×TBEB buffer for 5 minutes.

14. Reduce the volume of the eluted sample to 5 µL by speed-vac.

High-Fidelity PCR

1. For mutation detection of fractions down to $5 \times 10^4$ measure the copy number of the target APC sequence in the sample as described.

2. Add 25 µL of the 2×PCR master mix, the internal standard mutant at a desired fraction, and 2 µL of Pfu DNA polymerase to 1 µg of the sample. Bring the total reaction volume to 50 µL with dH$_2$O and mix thoroughly. Proceed to step 3.

3. For mutation detection of fractions down to $10^{-6}$ add 5 µL of the 2×PCR master mix and 0.4 µL of Pfu DNA polymerase to the mutant-enriched sample and mix thoroughly.

4. After a brief centrifugation, transfer the PCR mixture to either a 10 or 50 µL glass capillary tube by capillary action and seal both ends of the tube by heating in a gas flame.

5. Amplify the target sequence with an appropriate number of cycles to convert all the primers into product. For the target APC sequence, each PCR cycle proceeds in the order of 10 s at 94° C., 20 s at 50° C., and 20 s at 72° C. with 2 minutes at 94° C. and 2 minutes at 72° C. before and after the desired number of PCR cycles.

6. Cut both ends of the glass capillary tube with a glass-cutter and transfer the PCR product into a microcentrifuge tube. During the last few PCR cycles, the abundant mutant sequences form heteroduplex DNA with the excess wild-type fragments.

7. Incubate the PCR product at 72° C. for 20 minutes with additional Pfu DNA polymerase (0.2 µL Pfu/10 µL of PCR product).

Post-PCR Mutant Enrichment

1. Prepare CDCE set up as described with a 21 cm long coated capillary of 75 µm id.

2. Replace the 5% linear polyacrylamide matrix (about 2 µL) within the capillary.

3. Remove the buffer reservoir from the cathodic end of the capillary and place both a platinum wire and the capillary end into a microcentrifuge tube containing the PCR product (diluted 10-fold in dH$_2$O). Electrokinetically inject the PCR product at 2 µA for 30 s into the capillary. Remove the sample tube from the capillary end and reinsert the capillary end into the buffer reservoir. Perform electrophoresis at 9 µA.

4. Stop the electrophoresis just before the PCR-amplified mutant heteroduplexes reach the anodic end of the capillary and remove the buffer reservoir from the capillary end. Electroelute the heteroduplexes in 10 µL of 0.1× TBEB elution buffer at 9 µA for about 2–3 minutes using a platinum wire.

5. Take 5 µL of the electroeluted sample and add 5 µL, of 2×PCR master mix and 0.4 µL of Pfu DNA polymerase. Perform the PCR. A typical mutant enrichment is approximately 20-fold.

6. Repeat steps 2–5. Another 5-fold mutant enrichment can be achieved, bringing the total enrichment to approx 100-fold.

7. Take 1 µL of the PCR product and add 5 µL of 2×PCR master mix, 3.6 µL of dH$_2$O and 0.4 µL of Pfu DNA polymerase. Amplify the target sequence with 3 PCR cycles to convert all the mutant sequences into homoduplexes.

Mutational Spectra Display

1. Prepare the CDCE apparatus with a 33 cm coated capillary of 75 µm id and a 19 cm water jacket, as described. Set the water jacket circulator to the optimal temperature for separation of mutant from wild-type homoduplexes.

2. Replace the 5% linear polyacrylamide matrix within the capillary.

3. Electroinject the PCR product, diluted 10-fold in H20, and perform electrophoresis at 5 µA.

4. Measure the individual mutant fraction. The measurement is done by comparing the ratio of the area under each mutant peak to the area under the internal standard peak added to the sample.

Individual Mutant Purification for Sequencing

1. Purify each separated mutant homoduplex by PCR and by CDCE.

2. Identify each purified mutant by sequencing.

Notes

1. Care should be taken to maximize the transferred volume of the supernatant and to avoid the transfer of the pellet at the bottom of the tube and the top layers of the supernatant.

2. Avoid over-drying the DNA spool since a spool air-dried too long may be difficult to dissolve in 0.1×TE buffer.

3. The established protocol for target sequence enrichment requires a prior restriction digestion to liberate a target sequence desired from genomic DNA, as described in. A set of endonucleases for this restriction digestion should be selected to minimize the cost since digestion of genomic DNA from $10^8$ cells (~600 µg) for mutation detection at fractions down to $10^{-6}$ requires at least 600 U of the endonucleases. For the target APC sequence, HaeIII and XbaI were selected to liberate the sequence-embedded 482 bp fragment (APC cDNA bp 8422–8903) from genomic DNA at as low a cost as any other pair of restriction endonucleases available commercially.

4. When primers are completely depleted during PCR the copy number of the sequence amplified is equivalent to the initial copy number of the primers. The expected concentration of the PCR-amplified mutant internal standard is $10^{11}$ copies/μL upon complete conversion of the primers into product.

5. The amplification efficiency of the wild-type and mutant internal standard sequences must be the same. Unequal amplification efficiency of the wild-type and mutant will introduce errors in the measurement of the target sequence copy number and mutant fractions in the samples.

6. An optimal hybridization temperature needs to be determined for each probe-target sequence set. This temperature can be determined experimentally by measuring the target sequence recovered at different temperatures tested.

7. One end of an artificial clamp prepared must be complementary to the restriction end of a target sequence (DdeI restriction end for the target APC sequence).

8. Incubation longer than 4 hours and at temperatures above 37° C. should be avoided.

9. A second set of restriction endonucleases is necessary to excise the target sequence from the somewhat longer restriction fragment containing the target sequence (see Note 3). The cost of restriction endonucleases is no longer an important factor since the sample has been enriched for the target sequence by $10^4$-fold. Restriction digestion of a 482 bp fragment with AccI and Sau3AI liberates a 271 bp fragment (APC cDNA bp 8434–8704) that is suitable for pre-PCR mutant enrichment by CDCE.

10. The ionic strength of the sample buffer must be below that of 1×TBE for the electroinjection of an entire DNA sample. Ions are preferentially loaded before DNA onto the capillary.

11. An optimal CDCE separation temperature for mutant enrichment is that at which mutant/wild-type heteroduplexes are well separated from the wild-type homoduplex. Such a CDCE separation temperature can be determined by CDCE test runs with fluorescein-labeled PCR product containing the wild-type homoduplex, an artificially created mutant homoduplex and wild-type/mutant heteroduplexes.

12. Changes in the acrylamide concentration of the matrix, the length of separation zone and the field strength of electrophoresis can affect CDCE separation efficiency. Modifying these CDCE operating conditions may be necessary to obtain the desired degree of CDCE separation.

13. Take care to avoid introducing air bubbles into the capillary.

14. The electroelution of CDCE and RTCE separated mutants from the capillary is determined empirically. The electrophoresis time for the electroelution of the mutant can be determined by CDCE and RTCE test runs with fluorescein-labeled PCR product (see Note 11).

15. The combination of CDCE and RTCE separated mutant electroelution allows about 100- to 200-fold mutant enrichment. CDCE is used to separate mutant/wild-type heteroduplexes from the wild-type homoduplex, whereas RTCE is used to separate the CDCE-eluted mutant heteroduplexes from residual wild-type sequences. The residual wild-type sequences, which can co-migrate with the mutant heteroduplexes in the CDCE, could have been generated by incomplete restriction digestion or during the duplex reannealing step.

16. For mutation detection at fractions down to $5 \times 10^{-4}$ in DNA sequences without a neighboring natural clamp, an artificial clamp can be attached to a desired sequence by a GC-primer during this PCR.

17. The efficiency and conditions of PCR need to be determined experimentally for each target sequence. Thus, the number of PCR cycles necessary to convert all the primers into product depends on a sequence of interest and starting copy numbers. Avoid applying more PCR cycles than necessary since it may cause PCR product degradation.

18. To reduce the amount of PCR-generated byproducts, post-PCR incubation is necessary for some target sequences.

19. For mutation detection at fractions down to $5 \times 10^{-4}$, 100-fold post PCR mutant enrichment allows CDCE visualization of mutants, separated from each other. A typical mutant with an initial fraction of $10^{-4}$ is enriched to a fraction of $10^{31\ 2}$ using the method described herein. For mutation detection at fractions down to $10^{-6}$, a 100-fold pre-PCR mutant enrichment (see Note 15) in addition to post-PCR mutant enrichment allows visualization of the CDCE separated mutants at initial fractions of $10^{-6}$ or higher.

Example 2

Measurement of MNNG-Induced Point Mutations in the APC Gene

A means has been developed to scan for point mutations in 100 bp nuclear single-copy sequences at mutant fractions as low as $10^{-6}$. Beginning with about $10^8$ human cells, the sample is first enriched for the desired nuclear sequence 10,000-fold from the genomic DNA by sequence-specific hybridization coupled with a biotin-streptavidin capture system. Enrichment for rare mutant sequences 100-fold against the wild-type sequence was achieved by wide-bore constant denaturant capillary electrophoresis (CDCE). The mutant-enriched sample was subsequently amplified by high-fidelity PCR (hifiPCR) using fluorescein-labeled primers. Amplified mutant sequences were further enriched via two rounds of CDCE coupled with hifiPCR. Individual mutants, seen as distinct peaks on CDCE, were then isolated and sequenced.

This approach was tested by measuring N-methyl-N'-nitro-N-nitrosoguanidine (MNNG) induced point mutations in an 121 bp sequence of the adenomatous polyposis coli (APC) gene in human lymphoblastoid MT1 cells. Twelve different MNNG-induced GC–>AT transitions were reproducibly observed in MNNG-treated cells at mutant fractions between $2 \times 10^{-6}$ and $9 \times 10^{-6}$. The sensitivity of this approach was limited by the fidelity of Pfu DNA polymerase, which created fourteen different GC–>TA transversions each at a mutant fraction equivalent to that around $10^{-6}$ in the original samples. The approach described herein will be general for all DNA sequences suitable for CDCE analysis because the sensitivity and capacity permits detection of stem cell mutations in tissue sectors consisting of about $10^8$ cells.

Materials and Methods

Human Cell Line and MNNG Treatment

Human lymphoblastoid MT1 cells are resistant to the toxicity but not the mutagenicity of MNNG, putatively because they are knockout mutants of the hMSH6 gene for mismatch repair. An exponentially growing culture consisting of $8\times10^7$ MT1 cells was treated with 4 μM MNNG (Sigma Chemicals, St. Louis, Mo.) for 45 minutes. After treatment, the cells were grown for 30 generations with daily dilution to dilute any unrepaired pre-mutagenic lesions that could be mistaken for mutations by the procedures described herein. Untreated cells grown in parallel cultures served as controls. Using a microtiter plate mutation assay and selecting for 6-thioguanine-resistant (6TGR) colonies, the MNNG-induced mutant fraction in the HPRT gene was measured to be $8\times10^{-3}$.

Preparation of Cellular DNA Enriched for the Desired APC Gene Fragment

Genomic DNA was isolated from over $3\times10^8$ MNNG-treated and untreated MT1 cells without exposing DNA to either phenol or anion-exchange resins. The genomic DNA was digested with HaeIII and XbaI (New England Biolabs, Beverly, Mass.) at 1U enzyme/μg DNA and 2–3 mg DNA/mL overnight to liberate the target sequence embedded in a 482 bp fragment representing the APC cDNA bp 8422 to 8903. The initial copy numbers of the APC target sequence and a 205 bp human mitochondrial DNA sequence (mitochondrial bp 10011–10215) in the restriction digestion were measured based on competitive PCR followed by CDCE separation. In brief, a small aliquot of the sample was mixed with known copies of an artificial mutant and subjected to PCR amplification. The PCR products were separated by CDCE. The areas under the wild-type, mutant and heteroduplex peaks were measured. The ratio of the amount of the wild-type sequence versus the artificial mutant in the PCR products was used to calculate the initial copy number of the target sequence. The APC artificial mutant used represented the APC cDNA bp 8422–8913 containing an AT–>GC transition at bp 8652. The mitochondrial artificial mutant represented the mitochondrial bp 10011–10215 with a TA–>CG at bp 10072. Based on the target copy number measured in the digestion sample, the APC artificial mutant was added to the sample at a precise mutant fraction to serve as an internal standard.

To enrich for the desired APC gene fragment, two 5'-biotinylated 30-mer probes BP1 (APC cDNA bp 8472–8501; 5'-CAA AAC TGA CAG CAC AGA ATC CAG TGG AAC-3'; SEQ ID NO.: 1) and BP2 (complementary to APC cDNA bp 8501–8530; 5'-AAG ACC CAG AAT GGC GCT TAG GAC TTT GGG-3'; SEQ ID NO.: 2) were added to the genomic DNA digestion at a probe/target molar ratio of $5\times10^4$ each. The positions of the two probes in the APC restriction fragment are shown in FIG. 2A. The probes were PAGE-purified and the biotin moiety was linked to each probe by an 18-carbon spacer arm. The sample was boiled for 2 minutes and immediately chilled in an ice bath for 10 minutes. Hybridization was then performed at 58° C. for 2 hours in 6×SSPE (1.08 M NaCl, 60 mM sodium phosphate, pH 7.4, 6 mM EDTA). The probe-target hybrids were captured by mixing with streptavidin-coated controlled porous glass paramagnetic beads (CPG, Lincoln Park, N.J.) at 0.4 mg beads/$10^8$ target copies at 50° C. for 1 hour. The beads were washed four times with washing buffer (1M NaCl, 10 mM Tris-HCl pH 7.6, 2 mM EDTA) at 10 mg beads/mL at 50° C. for 5 minutes. The desired probe-bound DNA was recovered by twice washing the beads with deionized $H_2O$ at 20 mg beads/mL at 70° C. for 2 minutes. The copy numbers of the APC target sequence and the mitochondrial DNA sequence in the elution were measured to estimate the yield and enrichment of the target sequence.

The elution was concentrated to 10 μL by speed-vac centrifugation and reannealed at 55° C. for 16 hours in 0.2 M NaCl, 10 mM Tris-HCl pH 7.6), 2 mM EDTA buffer. This reannealing converted all rare mutant sequences into the mutant/wild-type heteroduplexes in the presence of an excess of wild-type sequences, which was necessary for efficient separation of mutants from wild-type DNA based on differences in the melting temperature. The reannealed DNA was digested with Sau3AI and AccI (New England Biolabs, Beverly, Mass.) to excise the desired 271 bp APC fragment (APC cDNA bp 8434–8704) suitable for CDCE analysis (FIG. 2B). The sample was then desalted and concentrated through ultrafiltration using a Microcon-50 concentrator (Amicon, Beverly, Mass.).

Constant Denaturant Capillary Electrophoresis

A CDCE instrument using laser-induced fluorescence detection system was utilized. The inner surfaces of fused silica capillaries (Polymicro Technologies, Phoenix, Ariz.) were coated with 6% linear polyacrylamide. Electrophoresis was performed in a piece of coated capillary (21–33 cm) filled with a 5% linear polyacrylamide matrix in 1×TBE (89 mM Tris-borate, 1 mM EDTA, pH 8.3). The matrix was replaced before each run. A portion of the capillary near its inlet was heated by a temperature-controlled water jacket (6–10 cm) where DNA sequences with even a single bp substitution could be separated based on differences in the melting temperature. The detection window on the capillary was positioned 7 cm from its outlet (the anode end).

The target-enriched cellular DNA sample was separated by CDCE using a 19.5 cm long, 540 μm ID capillary and a 6 cm water jacket at a temperature of 66.0° C. CDCE-purified wild-type APC fragments were also run on CDCE to serve as a negative control. The DNA was electrokinetically loaded onto the column through a tightly mounted Teflon tubing. Electrophoresis was performed at a constant current of 80 μA. The desired mutant/wild-type heteroduplex fraction was electroeluted from the capillary outlet into 10 μL collecting buffer consisting of 0.8×TBEB (71 mM Tris-Borate, pH 8.3, 0.8 mM EDTA, 0.2 mg/mL BSA). The collected heteroduplex fraction from the cellular DNA sample was desalted by drop dialysis against 0.1×TBE and subjected to CE separation at room temperature. The fraction containing the 271 bp APC restriction fragment was electroeluted. The efficiency of mutant enrichment was determined by measuring the copy number of the target sequence loaded onto the capillary and that eluted in the mutant-enriched fraction.

PCR products were separated by CDCE using a 75 μm ID capillary. About $10^8$ copies of the target sequence were electroinjected. To separate the heteroduplexes from wild-type homoduplex, CDCE was performed in a 21 cm capillary at a constant current of 9 μA. A 6 cm water jacket at a temperature of 64.6° C. was used. The heteroduplex fraction was electroeluted into 10 μL of 0.1×TBEB buffer. To separate mutant homoduplexes, CDCE was run in a 33 cm capillary using a 19 cm water jacket. The initial mutant fraction of each mutant was determined by comparison of the area under the mutant peak to that of the internal standard. Mutant peaks were individually purified (through CDCE collection followed by PCR) and sequenced.

High-Fidelity PCR

HifiPCR was performed in 10–50-μL capillary tubes using native *Pyrococcus furiosus* (Pfu) DNA polymerase with an associated 3'->5' exonuclease activity (Stratagene, La. Jolla, Calif.) and an Air Thermo-Cycler™ (Idaho Technology, Idaho Falls, Id.). The PCR mixture contained 20 mM Tris-HCl (pH 8.0), 2 mM $MgCl_2$, 10 mM KCl, 6 mM $(NH_4)_2SO_4$, 0.1% Triton X-100, 0.1 mg/mL BSA, 0.1 mM dNTPs, 0.2 μM each primer, and 0.1 U/μL Pfu DNA polymerase.

The primer sequences for amplifying the APC gene target sequence were 5'-fluorescein labeled (APl: APC cDNA bp 8441–8460; 5'-GAA TAA CAA CAC AAA GAA GC-3'; SEQ ID NO.: 3; and AP4H: complementary to APC cDNA bp 8664–8683; 5'-AAC AAA AAC CCT CTA ACA AG-3'; SEQ ID NO.: 4). The reaction conditions were as follows: 94° C. for 2 minutes; an appropriate number of cycles, each cycle with 10 seconds at 94° C., 20 seconds at 50° C. and 20 seconds at 72° C.; and 72° C. for 2 minutes. The PCR products were then incubated with additional Pfu DNA polymerase (0.05 U/μL at 72° C. for 5 minutes) to remove interfering byproducts. To create mutant/wild-type heteroduplexes, a sufficient number of PCR cycles (based on the PCR efficiency of 0.5–0.6) was used to deplete the primers such that the mutants would reanneal with the excess wild-type sequence during the final cycles. To create mutant homoduplexes for the final CDCE display, aliquots of the PCR products were subjected to 3–6 cycles of PCR such that an excess of primers were still present in the final reaction.

The PCR conditions for amplification of the 205 bp human mitochondrial DNA sequence (mitochondrial bp 10011–10215) utilized the primers CW7 (mitochondrial bp 10011–10031; 5'-ACC GTT AAC TTC CAA TTA AC-3'; SEQ ID NO.: 9) and 5'-fluorescein-labeled J3 (complementary to mitochondrial bp 10196–10215; 5'-GCG GGC GCA GGG AAA GAG GT-3'; SEQ ID NO.: 10).

Limit to Sensitivity: PCR-Induced Noise

The background mutant peaks observed in the untreated MT1 samples were also found in the Pfu-PCR noise control using CDCE- purified wild-type DNA. Independent PCR experiments with CDCE-purified wild-type DNA and Pfu DNA polymerase further demonstrated that the mutant fraction of the set of background mutations increased linearly with the number of PCR doublings, indicating that these mutations arose predominantly from the PCR process itself as opposed to DNA lesions generated prior to PCR. The total background mutant fraction in the final PCR products of the untreated MT1 samples was measured to be $4.6 \times 10^{-3}$, given that the internal standard was present at $10^{-3}$ after pre-PCR mutant enrichment. The Pfu DNA polymerase error rate for the 121 bp APC target sequence was thus estimated to be $1.8 \times 10^{-6}$ mutations per bp per doubling (=$4.6 \times 10^{-3}$ mutations/(121 bp×21 doublings)). A further increase in sensitivity of this approach will require an improved pre-PCR mutant enrichment and/or polymerase fidelity.

The fourteen identified low $T_m$ background mutations, which represented about 50% of the total PCR-induced mutations in the APC target sequence, were exclusively GC–>TA transversions (FIG. 5). Transversions have been previously identified as the predominant Pfu-induced mutational hotspots in a 100-bp human mitochondrial DNA sequence. The Pfu DNA polymerase mutational spectra observed in these two templates are markedly different from the spectra reported for other DNA polymerases (including Taq, Klenow fragment, Vent, T4 and modified T7), which are dominated by transition mutations. This difference may reflect the unique properties of Pfu DNA polymerase, namely, proofreading and/or mispair extension.

MNNG-Induced Mutational Spectrum in the APC Gene Target Sequence in MT1 Cells

Distinct from the background mutations in the untreated controls, twelve GC–>AT transitions were reproducibly observed in the MNNG-treated cells at mutant fractions ranging from $2.2 \times 10^{-6}$ to $9.2 \times 10^{-6}$ (FIGS. 4, 5 and 6). The transitions were predominantly found at guanine residues flanked by a purine, particularly at their 5' position (Table 2). It is unlikely that the CDCE-based method could preferentially enrich and/or separate transitions at these sites, because no bias in favor of 5' PuG sites is seen for the spontaneous GC–>AT transitions detected in a 100-bp human mitochondrial DNA sequence using a similar approach.

The results with regard to the kind of mutation induced by MNNG and its site specificity agree with previous observations in *E. coli*, yeast and other human systems. It has been suggested that the neighboring nucleotides may influence the distribution of $O_6$-methylguanine lesions by modifying the reactivity of the $O_6$ position of guanine and/or the replication and repair process. All of the previous studies, however, were based on phenotypic selection; hence, it was argued that the non-random distribution of MNNG-induced mutation in some targets could be a reflection of the influence of the mutation on protein structure and function. For example, a GC–>AT transition in the Gly (5'-GGN-3') and Trp (5'-UGG-3') codon sequences is more likely to be selected as a hotspot because Gly residues are often strategic to protein structure and the transition in Trp coding sequence results in a translation termination signal. Results described herein clearly show that the observed site specificity of MNNG-induced mutation is independent of phenotypic selection.

Example 3

Protocol for Enriching Multiple Target Sequences from the Same Digested Human Genomic DNA Sample Human genomic DNA (gDNA) digested with BsmAI (5 cutter) and SspI (6 cutter).

Target sequences to be enriched:
1. p53 gene fragment containing exon 5: p53 gDNA bp 13044–13252, 209 bps. Probes used: p53-BP3 and p53-BP4
2. p53 gene fragment containing exon 7: p53 gDNA bp 13960–14502, 543 bps. Probes used: p53-BP1 and p53-BP2
3. HPRT gene fragment containing exon 7: HPRT gDNA bp 39786–39950, 165 bps. Probes used: hprt-BP1 and hprt-BP2
4. $K_1$-ras gene fragment containing exon 1: bp positions not determined. Probes used: ras-BP1 and ras-BP2.

Overview of the Protocol:

Two pairs of biotin-labeled probes that are specific for the p53 exon 7 and Hprt exon 7 fragment are immobilized onto streptavidin-coated paramagnetic and non-magnetic beads, respectively. The restriction digested gDNA is denatured and allowed to hybridize simultaneously to the pair of probes bound on the two types of beads. After the hybridization, the beads (both paramagnetic and non-magnetic) are separated from the bulk DNA solution by centrifugation. The beads are washed and the washes are combined with the bulk DNA solution. The paramagnetic beads are then magnetically separated from the nonmagnetic beads. The desired target sequences, p53 exon 7 and Hprt exon 7 fragment, are then separately eluted by heating from the paramagnetic beads and nonmagnetic beads, respectively.

The bulk DNA solution is recycled for enriching two other gDNA fragments, p53 exon 5 and $K_1$-ras exon 1, in the same manner as described above.

Protocol:
1. Wash appropriate amounts of streptavidin-coated paramagnetic beads (CPG, Inc., Lincoln Park, N.J.) and streptavidin-coated colored non-magnetic beads (Bangs Laboratories, Inc., Fishers, Ind.) with 3×SSPE. Use 0.2 mg of beads for digestion containing 10–20 µg gDNA if the digestion volume is less than 250 µL; double the amount of beads for digestion of 250–500 µL; triple the amounts of beads for digestion of 500–700 µL. Use 0.6 mg of beads for digestion containing 60 µg of DNA. The paramagnetic beads are separated from the solution magnetically, the non-magnetic beads are separated from the solution by centrifugation at 14,000 rpm for 5 to 10 minutes.
2. Resuspend the paramagnetic beads in 3×SSPE buffer with probes hprt-BP1 and hprt-BP2, and the non-magnetic beads with probes P53-BP1 and P53-BP2. Use 1 µL of each probe (20 µM) per 0.2 mg of beads. Mix in a thermomixer at room temperature for 30 minutes.
3. Meanwhile, denature the digested gDNA sample in boiling water for 2 minutes. Chill the sample immediately in an ice-bath for 10 minutes.
4. Wash the probe-bound beads three times each with 3×SSPE at a concentration of 10 mg beads/mL at room temperature.
5. Resuspend 0.2 mg of the probe-bound paramagnetic and non-magnetic beads in the denatured sample (0.4 or 0.6 mg beads per sample if the sample volume exceeds 250 or 500 µL, respectively). Add 20×SSPE to the sample to a final concentration of 6×SSPE
6. Incubate the sample in a thermomixer at 50° C. for 2 hours, rotating at maximum speed.
7. Separate the beads from the bulk DNA solution by centrifugation at 14,000 rpm for 10 minutes.
8. Wash the beads twice each with 6×SSPE at 10 mg of beads/mL at 50° C. for 5 minutes. Combine the washes with the bulk DNA solution.
9. Rinse the beads at room temperature with 1×SSPE and 0.3×SSPE respectively, and magnetically separate the paramagnetic beads from the nonmagnetic beads. Repeat this procedure until the two types of beads are completely separated.
10. Resuspend the beads in ddH$_2$O at 20 mg beads/mL. Elute the target-enriched DNA from the beads at 72° C. for 2 minutes. Separate the elution from the beads. Repeat the elution step once and combine the two elutions.
11. Store the elutions and the bulk DNA solution at −20° C. before the next steps.
12. Immobilize probes ras-BP1 and ras-BP2 on the paramagnetic beads, and probes P53-BP3 and P53-BP4 on the nonmagnetic beads as described in Steps 1 and 2.
13. Wash the probe-bound beads three times with 3×SSPE at a concentration of 10 mg beads/mL at room temperature.
14. Resuspend 0.2 mg of both probe-bound beads in the bulk DNA sample from Step 11 (0.4 or 0.6 mg beads per sample if the initial volume of the digestion exceeds 250 or 500 µL, respectively).
15. Hybridize in a thermomixer at 45° C. for 2 hours, rotating at the maximum speed.
16. Repeat Steps 7–11 to obtain elutions containing enriched K$_1$-ras and p53 gene sequences, respectively.

Results

The above protocol was applied to over 200 gDNA samples that were extracted from dissected human bronchial epithelium sectors. The copy number of each target sequence was measured in the original DNA digest and the target-enriched elution sample using competitive PCR followed by CDCE separation. The recovery of the target sequence, defined as the ratio of the target copy number in the target-enriched sample versus that in the original digest, was determined to be greater than 70% for each of the four target sequences in all of the gDNA samples processed.

Example 4

Measurement of the Number of Point Mutations by Allele-Specific PCR Coupled with Target Enrichment To investigate the role of cigarette smoking in lung carcinogenesis, the number and mutant fraction of four nuclear point mutations in apparently normal postmortem lungs of two smokers and two nonsmokers were measured. Among the four mutations chosen for the analysis, three were G–>T transversions at bp 746 and 747 of the p53 gene (GenBank accession number: NM000546) and bp 129 of the K-ras gene (GenBank accession number: L00045), respectively. All three mutations were previously reported mutational hotspots in human lung carcinoma. The upper bronchial tree consisting of $7 \times 10^7$ to $40 \times 10^7$ epithelial cells from each lung was dissected into approximately 50 microanatomically distinct sectors of about 1 to 5 million cells each. DNA sequences comprising the seventh exon of the p53 gene, the first exon of the K-ras gene and the seventh exon of the HPRT gene were extracted from digested genomic DNA of each sector using sequence-specific hybridization in combination with biotin-streptavidin capture systems (see Example 1).

Allele-specific PCR assays for G–>T transversions were performed on each sector sample at bp 746 and 747 of the p53 gene and bp129 of the K-ras gene, and for a G–>A transition at bp 508 of the HPRT gene (GenBank accession number: M26434). Allele-specific PCR was performed using Taq DNA polymerase and allele-specific primers under optimized PCR conditions. Each allele-specific primer was designed in such a way that it contained two mismatches with the wild-type sequence at the primer's 3' ultimate and penultimate positions, but one mismatch with the mutant sequence at the primer's 3' penultimate position. Under optimized PCR conditions, the allele-specific primer, paired with a perfect matched FITC-labeled primer, allowed preferential amplification of the mutant sequence with an efficiency of 100 to 1000-fold higher than that of the wild-type sequence. The allele-specific PCR products of the target sequences were analyzed by capillary gel electrophoresis separation coupled with laser-induced fluorescence detection.

Figure 7:
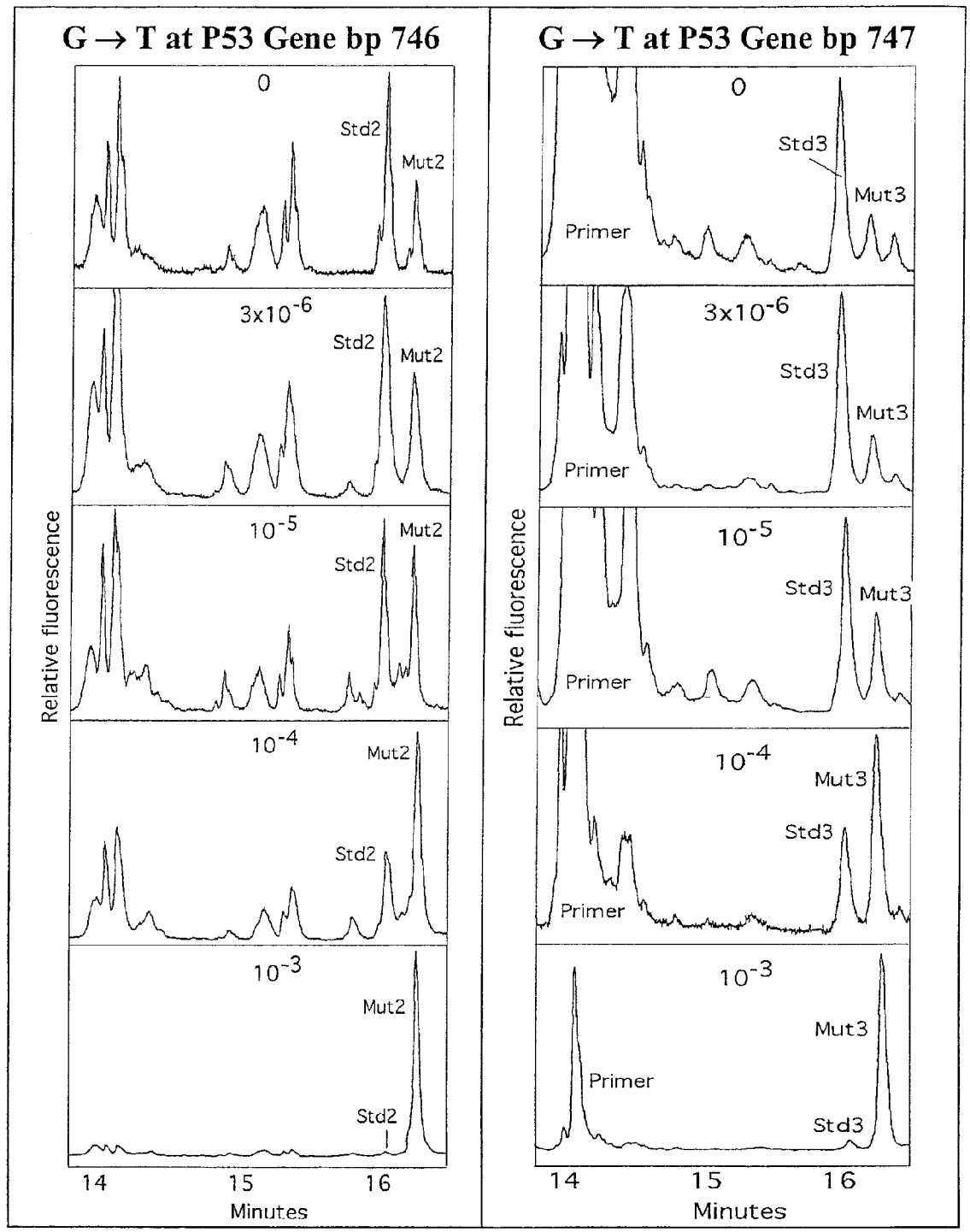
FIG. 7 is a graphical representation of CE separations of fluorescein-labeled mismatch amplification products from cellular DNA mixtures containing $2 \times 10^6$ copies of wild-type p53 sequence and various amounts of mutant at mutant factions of 0, $3 \times 10^{-6}$, $10^{-5}$, $10^{-4}$ and $10^{-3}$, respectively. The same amount (about 50 copies) of mutant internal standard fragments were introduced into each sample prior to the PCR. "Mut2" and "Std2" indicate the peaks amplified from the cellular DNA templates and internal standard using the mismatch primer specific for G->T at bp 746, respectively. "Mut3" and "Std3" indicate the peaks amplified using the mismatch primer specific for G->T at bp 747. The wild-type p53 exon7 fragments were isolated from TK6 cells, and mutant fragments were from human lung cancer cell lines containing the specific p53 mutations. The signals representing the G->T mutations at mutant fractions at or above $10^{-5}$ can be clearly distinguished from the background signals. Similar MAMA sensitivity was also achieved for G->T at bp 733 of p53.
Figure 8:
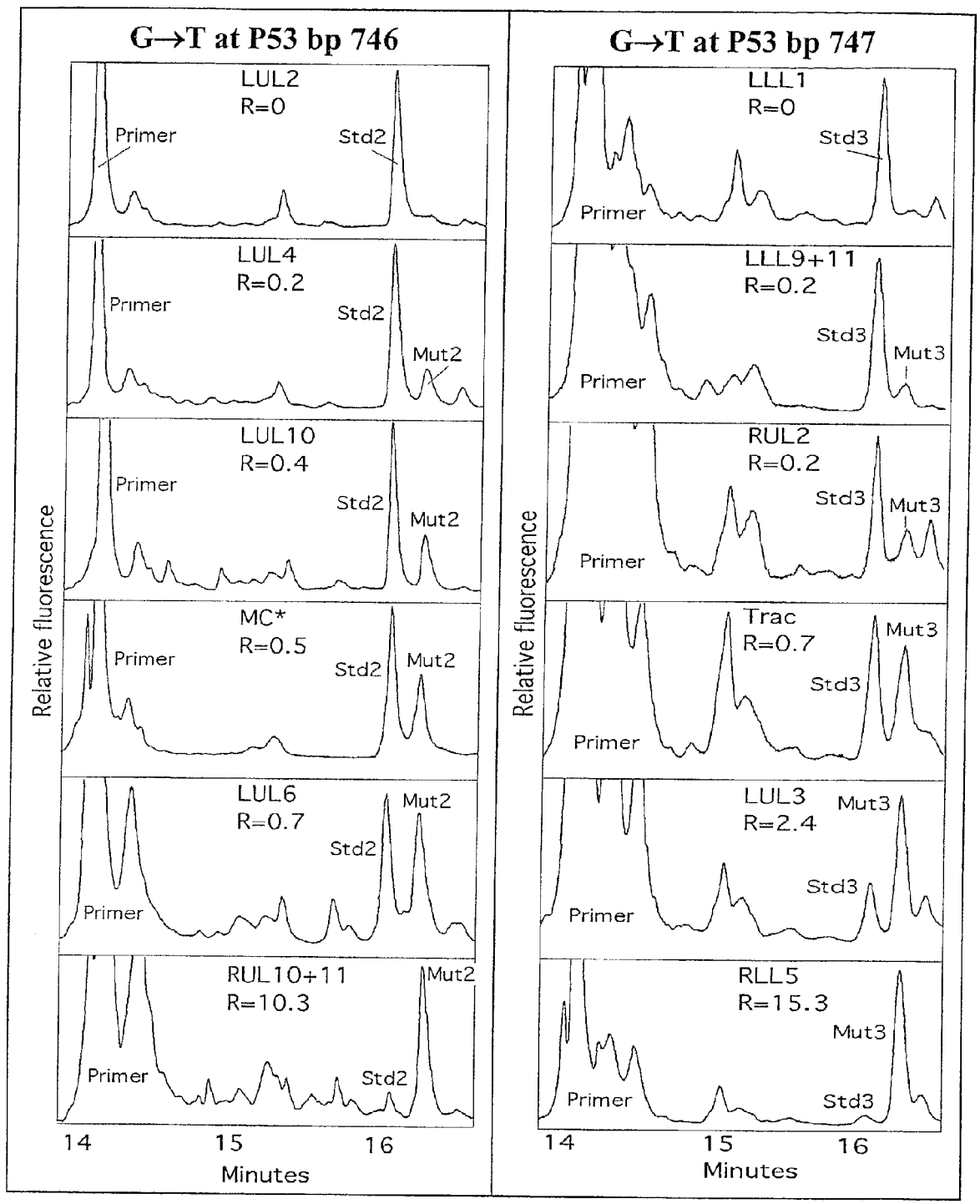

The results of the assays are shown for the G–>T transversions at bp 746 and 747 of p53 can be seen in FIG. 7. The assays were able to detect the p53 mutations occurring at mutant fractions at or above $10^{-5}$, or 20 mutants admixed with $2 \times 10^6$ copies of wild-type sequences. For each assay, known copies of an internal standard, which consists of the p53 mutation of interest and a 9 bp deletion, were introduced into the target-enriched sample and co-amplified with the original mutant sequences in each lung epithelium sector. As shown in FIG. 8, the initial copy number of mutants in each lung sector analyzed was determined based on 1) the ratio of the area under the mutant peak to that under the internal standard; 2) the background amplification from the wild-type sequence ($10^{-5}$ of the copies of the wild-type sequences); and 3) the fraction of the sector that was subjected to the assay. The assays for the G–>T mutations at bp 746 and 747 p53 were applied to the 210 lung sectors obtained from two smokers and two nonsmokers. The distributions of the number of mutants among the sectors of each lung were shown in FIGS. 9 and 10. Tables 3 and 4 summarize the number of p53 mutant colonies and average mutant fraction in the lungs analyzed.

TABLE 3

Characteristics of the lung samples analyzed.

| Lung | Smoking status (cigarettes/day × years) | Sex | Age | Cause of death | No. of cells (×10$^7$) | No. of sectors |
|---|---|---|---|---|---|---|
| Nonsmoker I | 0 | F | 55 | Stroke | 9 | 52 |
| Nonsmoker II | 0 | M | 50 | SHC[1] | 42 | 50 |
| Smoker I | 30 × 25 | F | 58 | Stroke | 28 | 41 |
| Smoker II | 30 × 26 | M | 47 | SHC | 7 | 67 |

[1]SHC, subarachnoid hemorrhage

TABLE 4

Summary of the number of p53 mutant colonies and average mutant fraction in the lungs analyzed.

| | No. of sectors with p53 mutants at | | Average MF/lung (×10$^{-5}$) | |
|---|---|---|---|---|
| Lung | bp 746 | bp 747 | bp 746 | bp 747 |
| Nonsmoker I | 46 | 40 | 6.4 | 2.9 |
| Nonsmoker II | 29 | 32 | 2.0 | 1.4 |
| Average of nonsmokers | 38 | 36 | 4.0 | 2.1 |
| Smoker I | 36 | 41 | 3.7 | 6.7 |
| Smoker II | 54 | 58 | 5.3 | 10.7 |
| Average of smokers | 45 | 50 | 5.4 | 8.4 |
| Average of all donors | 41 | 43 | 4.7 | 5.3 |

Example 5

Simultaneously Enriching Four Target Sequences from the Same Digested Human Genomic DNA Sample Human genomic DNA is digested with endonucleases BsmAI (5-cutter) and SspI (6-cutter).

Target sequences to be enriched are:
1. p53 gene fragment containing exon 5: p53 gDNA bp 13044–13252, 209 bps (GenBank accession number: NM000546). Probes used: p53-BP3 and p53-BP4
2. p53 gene fragment containing exon 7: p53 gDNA bp 13960–14502, 543 bps. Probes: p53-BP1 and p53-BP2
3. HPRT gene fragment containing exon 7: HPRT gDNA bp 39786–39950, 165 bps (GenBank accession number: NM000194). Probes: hprt-BP1 and hprt-BP2
4. K,-ras gene fragment containing exon 1: bp positions not determined. Probes: ras-BP1 and ras-BP2.

For each of the four specific target sequences, two biotin-labeled probes are used that are complementary to the Watson and Crick strand of the target sequence, respectively. The four probe pairs are pre-immobilized separately onto four types of streptavidin-coated microsphere beads labeled with different fluorescent colors. That is, p53-BP3 and p53-BP4 are immobilized on blue fluorescent beads, p53-BP1 and p53-BP2 on yellow-green fluorescent beads, hprt-BP1 and hprt-BP2 on red fluorescent beads, and ras-BP1 and ras-BP2 on orange beads.

The restriction digested gDNA is denatured and allowed to hybridize simultaneously to the probes bound to the four types of beads. After the hybridization, the beads are separated from the bulk DNA solution by centrifugation. The beads are washed and the washes are combined with the bulk DNA solution.

The four types of beads are then separated from each other using a commercially available fluorescent activated cell sorter (FACS). Currently, the most advanced flow cytometer (FACSVantage, Becton Dickinson) is capable of measuring up to five fluorescent parameters. This flow cytometer can sort microbeads at a rate of up to 15,000 microbeads per second with greater than 97% purity and a high recovery. After separation of the beads, the four target sequences are then eluted by heat denaturation from the corresponding type of beads in separate enriched pools. The depleted DNA solution is recycled for enriching a different set of target sequences.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method for detecting low frequency mutations in a target sequence from a DNA sample comprising the steps of:
   a) enriching a DNA sample for one or more target sequences, wherein the enrichment step comprises sequence-specific hybridization to the target sequences with one or more labeled probes, wherein each labeled probe is complementary to a specific target sequence, resulting in about a $10^3$-fold to about a $10^4$-fold enrichment of target sequences from the DNA sample thereby obtaining a target-enriched sample; and
   b) detecting mutations in the target sequence or sequences from the target-enriched sample.

2. The method of claim 1, wherein the enrichment step comprises:
   a) denaturing double-stranded DNA;
   b) contacting the denatured DNA with one or more probes comprising a sequence complementary to one or more target sequences to form a mixture;
   c) maintaining the mixture of step b) under conditions such that probe-fragment hybrid molecules are formed; and
   d) isolating the probe-fragment hybrids from the mixture, resulting in a target-enriched sample and a depleted sample.

3. The method of claim 2, wherein the DNA sample is fragmented prior to denaturation.

4. The method of claim 1, wherein a probe complementary to a specific target sequence comprises an affinity moiety unique for a specific target sequence.

5. The method of claim 1, wherein a plurality of target sequences is concurrently enriched from a sample resulting in a plurality of target-enriched DNA samples.

6. The method of claim 2, wherein the depleted sample is subjected to a subsequent enrichment step to enrich for one or more target sequences different from the target sequences obtained in the first enrichment step.

7. The method of claim 1, wherein the DNA sample comprises single-stranded DNA molecules.

8. The method of claim 1, wherein the DNA sample comprises double-stranded molecules.

9. The method of claim 1, wherein constant denaturant capillary electrophoresis is used to detect nuclear mutations.

10. The method of claim 1, wherein allele-specific polymerase chain reaction is used to detect nuclear mutations.

11. The method of claim 1, wherein the mutation detected is present at a mutant fraction about or higher than $10^{-6}$.

12. A method for detecting low frequency nuclear mutations in a target sequence from a genomic DNA sample comprising the steps of:
   a) enriching the DNA sample for molecules comprising one or more target sequences, thereby preparing a target-enriched sample comprising mutant and non-mutant sequences, wherein the enrichment step comprises sequence-specific hybridization with one or more labeled probes that hybridize to the target sequences resulting in about a $10^3$-fold to about $10^4$-fold enrichment of molecules comprising target sequences from the DNA sample;

b) subjecting the target-enriched sample to constant denaturant capillary electrophoresis using a wide-bore capillary to separate mutant heteroduplexes from non-mutant homoduplexes;
c) amplifying the heteroduplexes of step b) by high fidelity polymerase chain reaction to obtain amplified polymerase chain reaction products;
d) subjecting the polymerase chain reaction products of step c) to constant denaturant capillary electrophoresis to further enrich the sample for mutants, thereby creating a mutant-enriched sample;
e) subjecting the mutant-enriched sample of step d) to constant denaturant capillary electrophoresis to obtain a mutational spectra; and
f) selecting one or more individual mutant fractions from the mutational spectra for sequence analysis to detect mutations.

13. The method of claim 12, wherein step b) further comprises subjecting mutant heteroduplexes to capillary electrophoresis prior to high fidelity polymerase chain reaction.

14. The method of claim 12, wherein step d) further comprises subjecting the target-enriched sample to one or more additional rounds of con electrophoresis prior to obtaining the mutational spectra.

15. The method of claim 12, wherein the mutation detected is present at a mutant fraction about or higher than $10^{-6}$.

16. The method of claim 12, wherein step a) comprises fragmenting the genomic DNA to obtain double-stranded DNA fragments.

17. The method of claim 16, wherein a double-stranded DNA sample is enriched for one or more target sequences, said enrichment comprising the steps of:
   a) denaturing the double-stranded DNA;
   b) contacting the denatured DNA with a plurality of probes comprising a sequence complementary to one or more target sequences to form a mixture;
   c) maintaining the mixture of step b) under conditions such that probe-fragment hybrid molecules are formed; and
   d) isolating the probe-fragment hybrids from the mixture, resulting in a target-enriched sample and a depleted sample.

18. The method of claim 17, wherein the probe comprises an affinity moiety unique for a specific target sequence.

19. The method of claim 18, wherein the isolation of the probe-fragment hybrid is accomplished by contacting the probe-fragment hybrid with a binding partner molecule affixed to a solid support matrix, wherein the binding partner molecule binds to the affinity moiety of the probe.

20. The method of claim 19, wherein mutant heteroduplexes are subjected to capillary electrophoresis prior to hifiPCR.

21. The method of claim 19, wherein the enrichment further comprises one or more additional rounds of constant denaturant capillary electrophoresis prior to obtaining the mutational spectra.

22. A method of mutational analysis to detect nuclear gene mutations at mutant fractions at or above $10^{-6}$ in a target sequence comprising subjecting a DNA sample comprising one or more target sequences to constant denaturant capillary electrophoresis and high fidelity polymerase chain reaction to obtain a mutational spectrum to detect nuclear gene mutations, wherein, prior to constant denaturant capillary electrophoresis and high fidelity polymerase chain reaction, the DNA sample is enriched for a target sequence and wherein the enrichment comprises two steps wherein the first step comprises a sequence-specific hybridization coupled with a biotin-streptavidin capture system to enrich for DNA molecules comprising the target sequences, and wherein the second step comprises a mutant enrichment using constant denaturant capillary electrophoresis using a wide bore capillary.

23. The method of claim 22, wherein the double-stranded DNA fragments are enriched for fragments comprising one or more target sequence, said enrichment comprising the steps of:
   a) denaturing the double-stranded DNA fragments;
   b) contacting the denatured fragments with a probe comprising a sequence complementary to a known target sequence;
   c) maintaining the probe and DNA fragments under conditions such that a probe-fragment hybrid molecule is formed;
   d) isolating the probe-fragment hybrid; and
   e regenerating a double-stranded fragment, thereby generating an enriched pool of DNA fragments.

24. The method of claim 19, wherein the plurality of probes are affixed to a plurality of surfaces such that each surface comprises a single probe sequence, thereby specifically binding a specific target sequence.

25. The method of claim 24, wherein the plurality of surfaces are ordered such that a plurality of target sequences are enriched from a single DNA sample.

* * * * *

UNITED STATES PATENT AND TRADEMARK OFFICE
CERTIFICATE OF CORRECTION

PATENT NO. : 7,094,543 B2 Page 1 of 1
APPLICATION NO. : 10/265653
DATED : August 22, 2006
INVENTOR(S) : Xiao-Cheng Li-Sucholeiki, William G. Thilly and Elena Viktorovna Gostjeva It is certified that error appears in the above-identified patent and that said Letters Patent is hereby corrected as shown below:

Claim 14, column 39, line 24, delete "con" and insert -- constant denaturant capillary--.

Signed and Sealed this

Twenty-first Day of November, 2006

JON W. DUDAS
*Director of the United States Patent and Trademark Office*